(12) United States Patent
Remiszewski et al.

(10) Patent No.: US 9,495,745 B2
(45) Date of Patent: Nov. 15, 2016

(54) METHOD FOR ANALYZING BIOLOGICAL SPECIMENS BY SPECTRAL IMAGING

(71) Applicant: CIRECA THERANOSTICS, LLC, Parsippany, NJ (US)

(72) Inventors: Stanley H. Remiszewski, Spencer, MA (US); Clay M. Thompson, Camano Island, WA (US)

(73) Assignee: CIRECA THERANOSTICS, LLC, Parsippany, NJ (US)

(*) Notice: Subject to any disclaimer, the term of this patent is extended or adjusted under 35 U.S.C. 154(b) by 0 days.

(21) Appl. No.: 14/818,149

(22) Filed: Aug. 4, 2015

(65) Prior Publication Data

US 2016/0012591 A1    Jan. 14, 2016

Related U.S. Application Data

(63) Continuation of application No. 13/507,386, filed on Jun. 25, 2012, now Pat. No. 9,129,371, which is a continuation-in-part of application No. 13/067,777, filed on Jun. 24, 2011, now Pat. No. 9,025,850.

(60) Provisional application No. 61/358,606, filed on Jun. 25, 2010.

(51) Int. Cl.
| | |
|---|---|
| *G06K 9/00* | (2006.01) |
| *G06T 7/00* | (2006.01) |
| *G01N 21/31* | (2006.01) |
| *A61B 5/00* | (2006.01) |
| *G01N 21/3581* | (2014.01) |
| *G01N 21/35* | (2014.01) |

(52) U.S. Cl.
CPC .......... *G06T 7/0028* (2013.01); *G01N 21/314* (2013.01); *G06K 9/00127* (2013.01); *A61B 5/0071* (2013.01); *A61B 5/0075* (2013.01); *A61B 5/7257* (2013.01); *G01N 21/35* (2013.01); *G01N 21/3581* (2013.01); *G01N 2021/3595* (2013.01); *G06T 2207/30024* (2013.01)

(58) Field of Classification Search
None
See application file for complete search history.

(56) References Cited

U.S. PATENT DOCUMENTS

| | | |
|---|---|---|
| 1,996,141 A | 4/1935 | Broadhurst et al. |
| 5,945,674 A | 8/1999 | Dukor |

(Continued)

FOREIGN PATENT DOCUMENTS

| | | |
|---|---|---|
| JP | H11-283019 A | 10/1999 |
| JP | 3072948 B2 | 8/2000 |

(Continued)

OTHER PUBLICATIONS

A Japanese Office Action mailed Mar. 31, 2015 for corresponding Japanese Patent Application No. 2013-516834.

(Continued)

*Primary Examiner* — Nancy Bitar
(74) *Attorney, Agent, or Firm* — Arent Fox LLP

(57) ABSTRACT

A method for registering a visual image and a spectral image of a biological sample includes aligning a first set of coordinate positions of a plurality of reticles on a slide holder and a second set of coordinate positions of the plurality of reticles on the slide holder. The method further includes generating a registered image of a visual image of a biological sample and a spectral image of the biological sample based upon the alignment of the first and second set of coordinate positions.

16 Claims, 37 Drawing Sheets

(56) References Cited

U.S. PATENT DOCUMENTS

| | | | |
|---|---|---|---|
| 6,037,772 A | 3/2000 | Karczmar et al. | |
| 6,274,871 B1 | 8/2001 | Dukor et al. | |
| 6,348,325 B1 | 2/2002 | Zahniser et al. | |
| 6,661,501 B1 | 12/2003 | Zahniser et al. | |
| 6,665,060 B1 | 12/2003 | Zahniser et al. | |
| 6,697,507 B1 | 2/2004 | Chapman | |
| 6,841,388 B2* | 1/2005 | Dukor ............... | G01N 33/57415 250/339.02 |
| 7,006,674 B1 | 2/2006 | Zahniser et al. | |
| 7,496,220 B2 | 2/2009 | Izzia et al. | |
| 8,208,698 B2 | 6/2012 | Bogdan | |
| 8,598,998 B2* | 12/2013 | Vassilev ............... | A01M 29/16 340/384.2 |
| 8,736,685 B1* | 5/2014 | Dorenbosch ........... | H04N 17/02 348/187 |
| 9,008,407 B2* | 4/2015 | Tanji ...................... | G06T 5/002 250/227.23 |
| 2004/0131241 A1* | 7/2004 | Curry ................. | G01N 15/1468 382/133 |
| 2009/0226059 A1* | 9/2009 | Levenson ................ | G01N 1/30 382/128 |
| 2009/0326383 A1* | 12/2009 | Barnes ................. | A61B 5/0059 600/476 |
| 2010/0141752 A1 | 6/2010 | Yamada et al. | |
| 2010/0272334 A1 | 10/2010 | Yamada et al. | |
| 2011/0040169 A1 | 2/2011 | Kamen et al. | |
| 2012/0010528 A1* | 1/2012 | Donovan ............. | G06T 7/0081 600/567 |

FOREIGN PATENT DOCUMENTS

| | | |
|---|---|---|
| JP | 2003-513278 A | 4/2003 |
| JP | 2004-053498 A | 2/2004 |
| JP | 2005-058378 A | 3/2005 |
| JP | 2005-524072 A | 8/2005 |
| JP | 2005-331887 A | 12/2005 |
| JP | 2006-26015 A | 2/2006 |
| JP | 2006-026015 A | 8/2006 |
| JP | 2006-350098 A | 12/2006 |
| JP | 2008-533440 A | 8/2008 |
| JP | 2008-292195 A | 12/2008 |
| JP | 2009-297295 A | 12/2009 |
| JP | 2010-151830 A | 7/2010 |
| WO | WO 01/33215 A1 | 5/2001 |
| WO | WO 03/071729 A1 | 11/2003 |
| WO | WO 2006/083969 A2 | 8/2006 |
| WO | WO 2009/146425 A1 | 12/2009 |
| WO | WO 2010/046968 A1 | 4/2010 |
| WO | WO 2011/163624 A1 | 12/2011 |

OTHER PUBLICATIONS

International Search Report, dated Nov. 17, 2011, issued in International Patent Application No. PCT/US2011/041884.

Japanese Office Action mailed Mar. 31, 2015 for corresponding Japanese Patent Application No. 2013-516834.

Mexican Office Action, dated Aug. 26, 2014, corresponding to Mexican Patent Application No. MX/a/2012/015240.

Patent Examination Report, Australian Patent Application No. 2011270731 issued Dec. 11, 2013.

Supplementary European Search Report, dated Oct. 31, 2014, issued in the European Patent Application No. 12802249.8.

Japanese Office Action of related Japanese Patent Application No. 2014-517245 dated Apr. 12, 2016 (with English translation).

Japan Office Action of related Japanese Patent Application No. 2015-191282 dated Sep. 6, 2016.

* cited by examiner

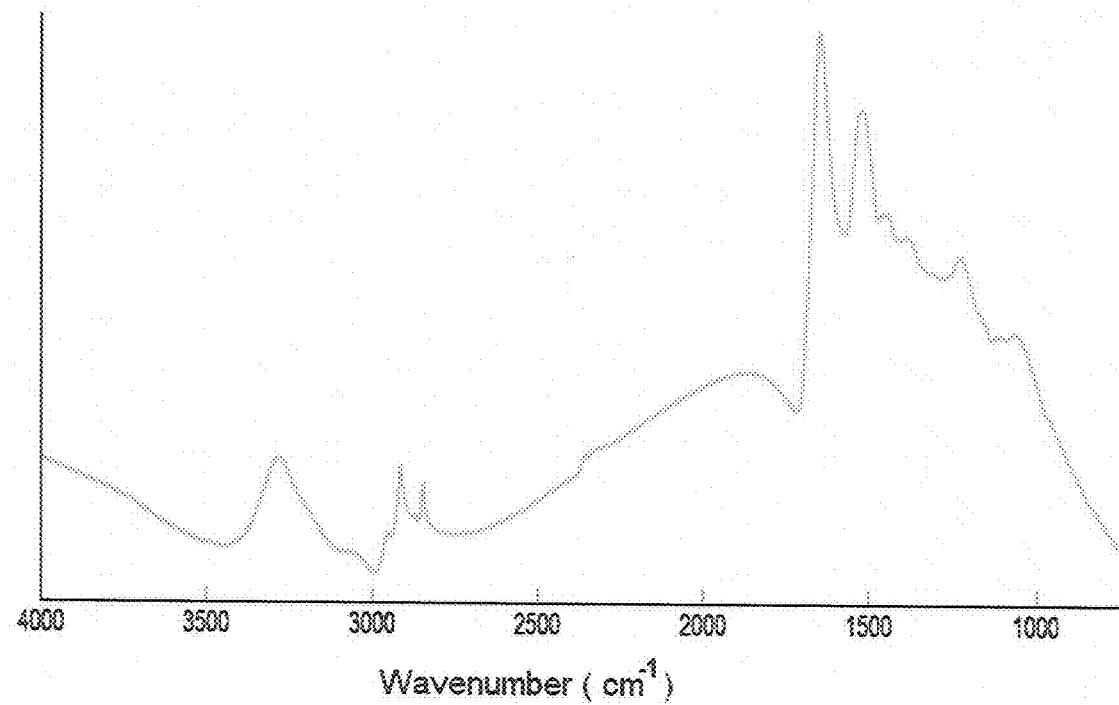

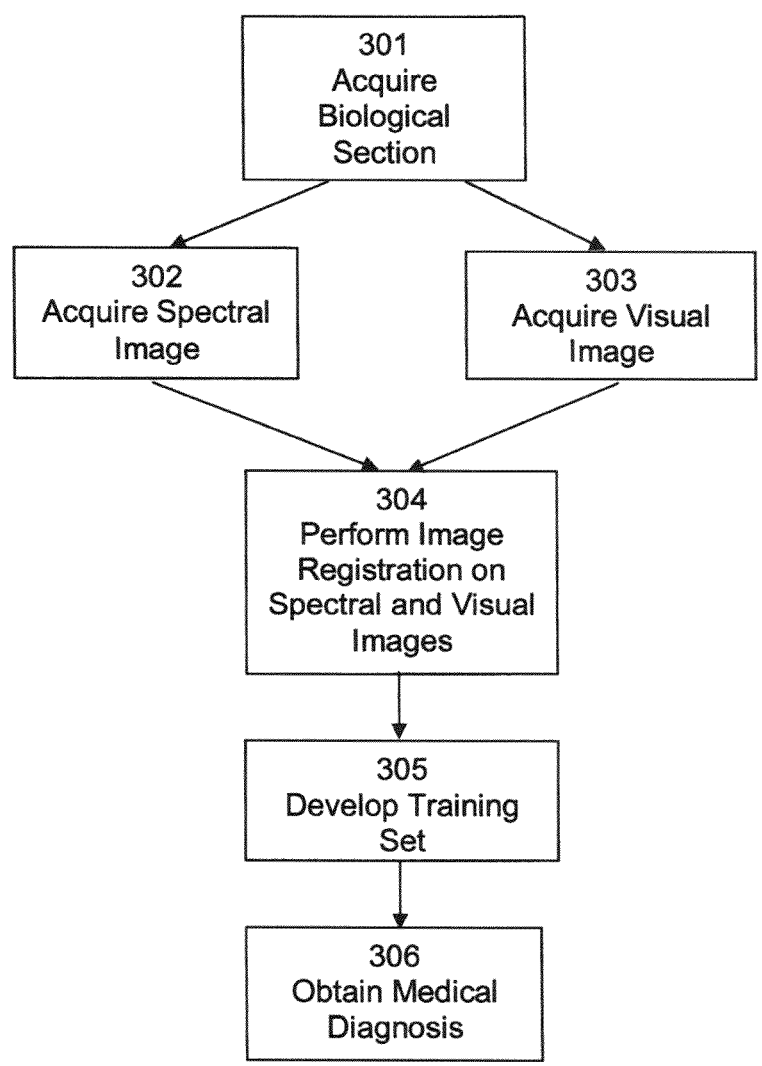

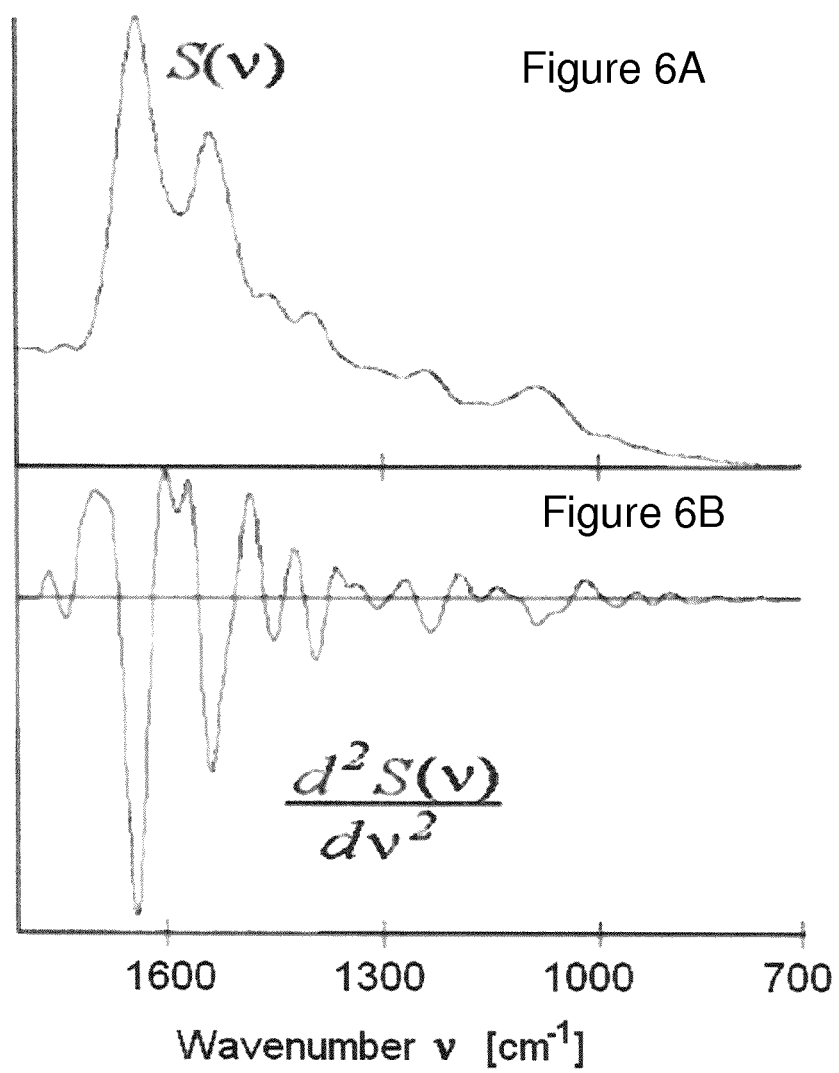

yellow   red   dark green

Figure 11A
Figure 11B
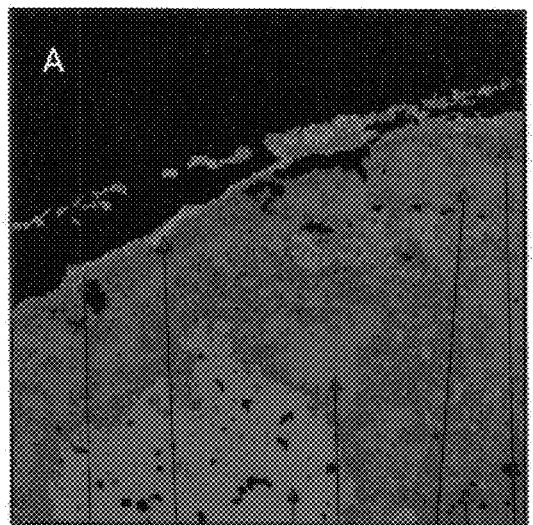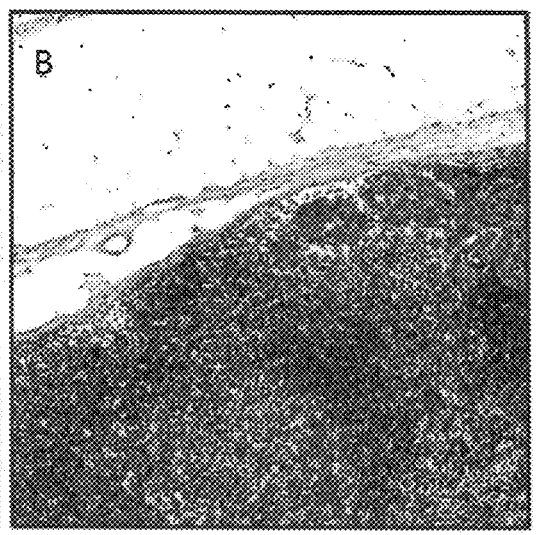
purple, light blue, light green, gray, red, blue, dark green Figure 13A
Figure 13B
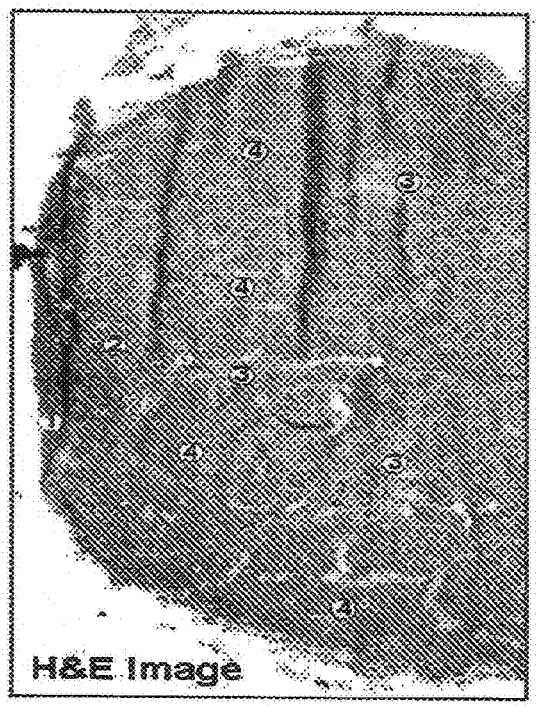

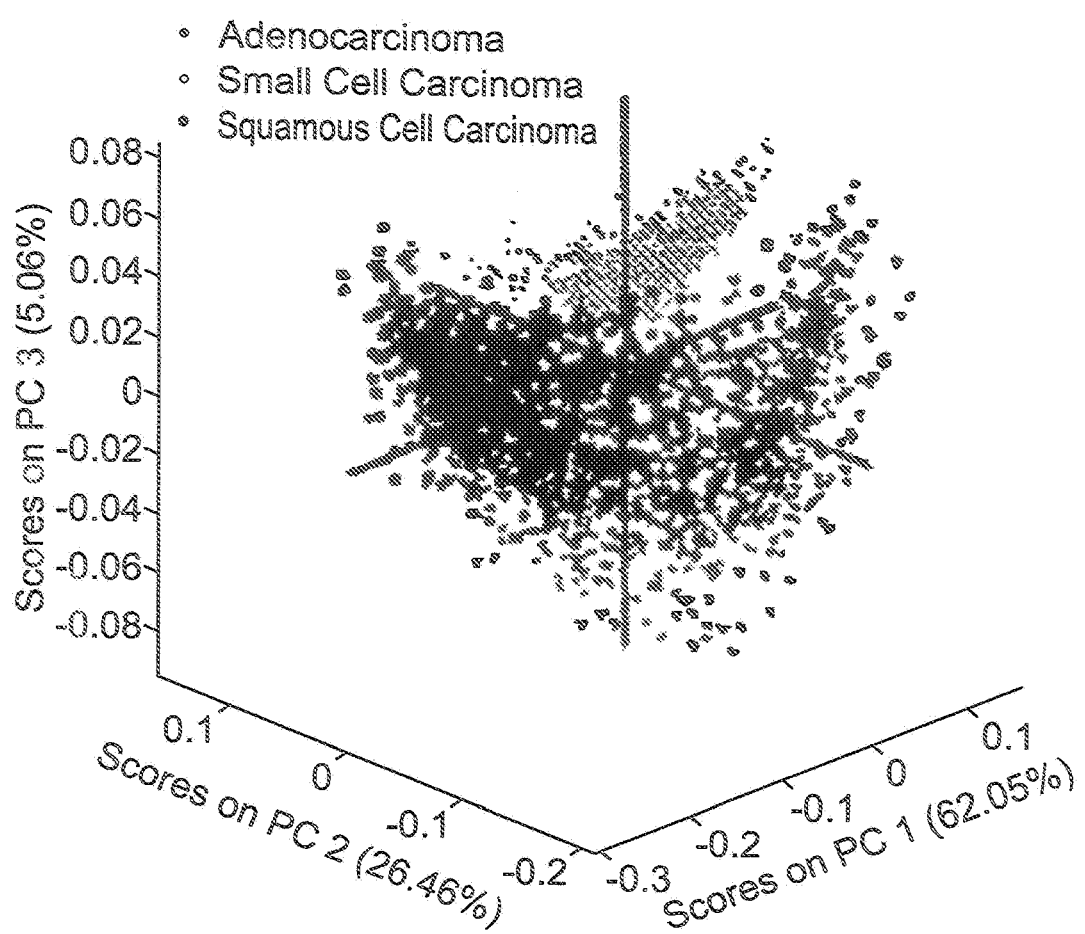

METHOD FOR ANALYZING BIOLOGICAL SPECIMENS BY SPECTRAL IMAGING

CROSS-REFERENCE TO RELATED APPLICATIONS

This application is a Continuation of U.S. patent application Ser. No. 13/507,386, filed Jun. 25, 2012, which is a Continuation-In-Part of U.S. patent application Ser. No. 13/067,777, filed on Jun. 24, 2011, which claims the benefit of U.S. Provisional Patent Application No. 61/358,606, filed on Jun. 25, 2010. The entirety of each of the foregoing applications is hereby incorporated by reference herein.

FIELD OF THE INVENTION

Aspects of the invention relate to a method for analyzing biological specimens by spectral imaging to provide a medical diagnosis, prognostic and/or predictive classification. The biological specimens may include medical specimens obtained by surgical methods, biopsies, and cultured samples.

BACKGROUND

Various pathological methods are used to analyze biological specimens for the detection of abnormal or cancerous cells. For example, standard histopathology involves visual analysis of stained tissue sections by a pathologist using a microscope. Typically, tissue sections are removed from a patient by biopsy, and the samples are either snap frozen and sectioned using a cryo-microtome, or they are formalin-fixed, paraffin embedded, and sectioned via a microtome. The tissue sections are then mounted onto a suitable substrate. Paraffin-embedded tissue sections are subsequently deparaffinized. The tissue sections are stained using, for example, an hemotoxylin-eosin (H&E) stain and are cover-slipped.

The tissue samples are then visually inspected at a high resolution visual inspection, for example, 10× to 40× magnification. The magnified cells are compared with visual databases in the pathologist's memory. Visual analysis of a stained tissue section by a pathologist involves scrutinizing features such as nuclear and cellular morphology, tissue architecture, staining patterns, and the infiltration of immune response cells to detect the presence of abnormal or cancerous cells.

If early metastases or small clusters of cancerous cells measuring from less than 0.2 to 2 mm in size, known as micrometastases, are suspected, adjacent tissue sections may be stained with an immuno-histochemical (IHC) agent/counter stain such as cytokeratin-specific stains. Such methods increase the sensitivity of histopathology since normal tissue, such as lymph node tissue, does not respond to these stains. Thus, the contrast between unaffected and diseased tissue can be enhanced.

The primary method for detecting micrometastases has been standard histopathology. The detection of micrometastases in lymph nodes, for example, by standard histopathology is a formidable task owing to the small size and lack of distinguishing features of the abnormality within the tissue of a lymph node. Yet, the detection of these micrometastases is of prime importance to stage the spread of disease because if a lymph node is found to be free of metastatic cells, the spread of cancer may be contained. On the other hand, a false negative diagnosis resulting from a missed micrometastasis in a lymph node presents too optimistic a diagnosis, and a more aggressive treatment should have been recommended.

Although standard histopathology is well-established for diagnosing advanced diseases, it has numerous disadvantages. In particular, variations in the independent diagnoses of the same tissue section by different pathologists are common because the diagnosis and grading of disease by this method is based on a comparison of the specimen of interest with a database in the pathologist's memory, which is inherently subjective. Differences in diagnoses particularly arise when diagnosing rare cancers or in the very early stages of disease. In addition, standard histopathology is time consuming, costly and relies on the human eye for detection, which makes the results hard to reproduce. Further, operator fatigue and varied levels of expertise of the pathologist may impact a diagnosis.

In addition, if a tumor is poorly differentiated, many immunohistochemical stains may be required to help differentiate the cancer type. Such staining may be performed on multiple parallel cell blocks. This staining process may be prohibitively expensive and cellular samples may only provide a few diagnostic cells in a single cell block.

To overcome the variability in diagnoses by standard histopathology, which relies primarily on cell morphology and tissue architectural features, spectroscopic methods have been used to capture a snapshot of the biochemical composition of cells and tissue. This makes it possible to detect variations in the biochemical composition of a biological specimen caused by a variety of conditions and diseases. By subjecting a tissue or cellular sample to spectroscopy, variations in the chemical composition in portions of the sample may be detected, which may indicate the presence of abnormal or cancerous cells. The application of spectroscopy to infrared cytopathology (the study of diseases of cells) is referred to as "spectral cytopathology" (SCP), and the application of infrared spectroscopy to histopathology (the study of diseases of tissue) as "spectral histopathology" (SHP).

SCP on individual urinary tract and cultured cells is discussed in B. Bird et al., Vibr. Spectrosc., 48, 10 (2008) and M. Romeo et al., Biochim Biophys Acta, 1758, 915 (2006). SCP based on imaging data sets and applied to oral mucosa and cervical cells is discussed in WO 2009/146425. Demonstration of disease progression via SCP in oral mucosal cells is discussed in K. Papamarkakis et al., Laboratory Investigations, 90, 589 (2010). Demonstration of sensitivity of SCP to detect cancer field effects and sensitivity to viral infection in cervical cells is discussed in K. Papamarkakis et al., Laboratory Investigations, 90, 589, (2010).

Demonstration of first unsupervised imaging of tissue using SHP of liver tissue via hierarchical cluster analysis (HCA) is discussed in M. Diem et al., Biopolymers, 57, 282 (2000). Detection of metastatic cancer in lymph nodes is discussed in M. J. Romeo et al., Vibrational Spectrosc., 38, 115 (2005) and M. Romeo et al., Vibrational Microspectroscopy of Cells and Tissues, Wiley-Interscience, Hoboken, N.J. (2008). Use of neural networks, trained on HCA-derived data, to diagnose cancer in colon tissue is discussed in P. Lasch et al., J. Chemometrics, 20, 209 (2007). Detection of micro-metastases and individual metastatic cancer cells in lymph nodes is discussed in B. Bird et al., The Analyst, 134, 1067 (2009), B. Bird et al., BMC J. Clin. Pathology, 8, 1 (2008), and B. Bird et al., Tech. Cancer Res. Treatment, 10, 135 (2011).

Spectroscopic methods are advantageous in that they alert a pathologist to slight changes in chemical composition in a biological sample, which may indicate an early stage of disease. In contrast, morphological changes in tissue evident from standard histopathology take longer to manifest, making early detection of disease more difficult. Additionally, spectroscopy allows a pathologist to review a larger sample of tissue or cellular material in a shorter amount of time than it would take the pathologist to visually inspect the same sample. Further, spectroscopy relies on instrument-based measurements that are objective, digitally recorded and stored, reproducible, and amenable to mathematical/statistical analysis. Thus, results derived from spectroscopic methods are more accurate and precise then those derived from standard histopathological methods.

Various techniques may be used to obtain spectral data. For example, Raman spectroscopy, which assesses the molecular vibrations of a system using a scattering effect, may be used to analyze a cellular or tissue sample. This method is described in N. Stone et al., Vibrational Spectroscopy for Medical Diagnosis, J. Wiley & Sons (2008), and C. Krafft, et al., Vibrational Spectrosc. (2011).

Raman's scattering effect is considered to be weak in that only about 1 in $10^{10}$ incident photons undergoes Raman scattering. Accordingly, Raman spectroscopy works best using a tightly focused visible or near-IR laser beam for excitation. This, in turn, dictates the spot from which spectral information is being collected. This spot size may range from about 0.3 µm to 2 µm in size, depending on the numerical aperture of the microscope objective, and the wavelength of the laser utilized. This small spot size precludes data collection of large tissue sections, since a data set could contain millions of spectra and would require long data acquisition times. Thus, SHP using Raman spectroscopy requires the operator to select small areas of interest. This approach negates the advantages of spectral imaging, such as the unbiased analysis of large areas of tissue.

SHP using infrared spectroscopy has also been used to detect abnormalities in tissue, including, but not limited to brain, lung, oral mucosa, cervical mucosa, thyroid, colon, skin, breast, esophageal, prostate, and lymph nodes. Infrared spectroscopy, like Raman spectroscopy, is based on molecular vibrations, but is an absorption effect, and between 1% and 50% of incident infrared photons are likely to be absorbed if certain criteria are fulfilled. As a result, data can be acquired by infrared spectroscopy more rapidly with excellent spectral quality compared to Raman spectroscopy. In addition, infrared spectroscopy is extremely sensitive in detecting small compositional changes in tissue. Thus, SHP using infrared spectroscopy is particularly advantageous in the diagnosis, treatment and prognosis of cancers such as breast cancer, which frequently remains undetected until metastases have formed, because it can easily detect micro-metastases. It can also detect small clusters of metastatic cancer cells as small as a few individual cells. Further, the spatial resolution achievable using infrared spectroscopy is comparable to the size of a human cell, and commercial instruments incorporating large infrared array detectors may collect tens of thousands of pixel spectra in a few minutes.

A method of SHP using infrared spectroscopy is described in Bird et al., "Spectral detection of micro-metastates in lymph node histo-pathology", J. Biophoton. 2, No. 1-2, 37-46 (2009), (hereinafter "Bird"). This method utilizes infrared micro-spectroscopy (IRMSP) and multivariate analysis to pinpoint micro-metastases and individual metastatic cells in lymph nodes.

Bird studied raw hyperspectral imaging data sets including 25,600 spectra, each containing 1650 spectral intensity points between 700 and 4000 $cm^{-1}$. These data sets, occupying about 400 MByte each, were imported and preprocessed. Data preprocessing included restriction of the wavenumber range to 900-1800 $cm^{-1}$ and other processes. The "fingerprint" infrared spectral region was further divided into a "protein region" between 1700 and 1450 $cm^{-1}$, which is dominated by the amide I and amide II vibrational bands of the peptide linkages of proteins. This region is highly sensitive to different protein secondary and tertiary structure and can be used to stage certain events in cell biology that depend on the abundance of different proteins. The lower wavenumber range, from 900 to 1350 $cm^{-1}$, the "phosphate region", contains several vibrations of the phosphodiester linkage found in phospholipids, as well as DNA and RNA.

In Bird, a minimum intensity criterion for the integrated amide I band was imposed to eliminate pixels with no tissue coverage. Then, vector normalization and conversion of the spectral vectors to second derivatives was performed. Subsequently, data sets were subjected individually to hierarchical cluster analysis (HCA) using the Euclidean distance to define spectral similarity and Ward's algorithm for clustering. Pixel cluster membership was converted to pseudo-color spectral images.

According to Bird's method, marks are placed on slides with a stained tissue section to highlight areas that correspond to areas on the unstained adjacent tissue section that are to be subjected to spectral analysis. The resulting spectral and visual images are matched by a user who aligns specific features on the spectral image and the visual image to physically overlay the spectral and visual images.

By Bird's method, corresponding sections of the spectral image and the visual image are examined to determine any correlation between the visual observations and the spectral data. In particular, abnormal or cancerous cells observed by a pathologist in the stained visual image may also be observed when examining a corresponding portion of the spectral image that overlays the stained visual image. Thus, the outlines of the patterns in the pseudo-color spectral image may correspond to known abnormal or cancerous cells in the stained visual image. Potentially abnormal or cancerous cells that were observed by a pathologist in a stained visual image may be used to verify the accuracy of the pseudo-color spectral image.

Bird's method, however, is inexact because it relies on the skill of the user to visually match specific marks on the spectral and visual images. This method is often imprecise. In addition, Bird's method allows the visual and spectral images to be matched by physically overlaying them, but does not join the data from the two images to each other. Since the images are merely physically overlaid, the superimposed images are not stored together for future analysis.

Further, since different adjacent sections of tissue are subjected to spectral and visual imaging, Bird's overlaid images do not display the same tissue section. This makes it difficult to match the spectral and visual images, since there may be differences in the morphology of the visual image and the color patterns in the spectral image.

Another problem with Bird's overlaying method is that the visual image is not in the same spatial domain as the infrared spectral image. Thus, the spatial resolution of Bird's visual image and spectral image are different. Typically, spatial resolution in the infrared image is less than the resolution of the visual image. To account for this difference in resolution, the data used in the infrared domain may be expanded by selecting a region around the visual point of interest and diagnosing the region, and not a single point. For every point in the visual image, there is a region in the infrared image that is greater than the point that must be input to achieve diagnostic output. This process of accounting for the resolution differences is not performed by Bird. Instead, Bird assumes that when selecting a point in the visual image, it is the same point of information in the spectral image through the overlay, and accordingly a diagnostic match is reported. While the images may visually be the same, they are not the same diagnostically.

To claim a diagnostic match, the spectral image used must be output from a supervised diagnostic algorithm that is trained to recognize the diagnostic signature of interest. Thus, the spectral image cluster will be limited by the algorithm classification scheme to driven by a biochemical classification to create a diagnostic match, and not a user-selectable match. By contrast, Bird merely used an "unsupervised" HCA image to compare to a "supervised" stained visual image to make a diagnosis. The HCA image identifies regions of common spectral features that have not yet been determined to be diagnostic, based on rules and limits assigned for clustering, including manually cutting the dendrogram until a boundary (geometric) match is visually accepted by the pathologist to outline a cancer region. This method merely provides a visual comparison.

Other methods based on the analysis of fluorescence data exist that are generally based on the distribution of an external tag, such as a stain or label, or utilize changes in the inherent fluorescence, also known as auto-fluorescence. These methods are generally less diagnostic, in terms of recognizing biochemical composition and changes in composition. In addition, these methods lack the fingerprint sensitivity of techniques of vibrational spectroscopy, such as Raman and infrared.

A general problem with spectral acquisition techniques is that an enormous amount of spectral data is collected when testing a biological sample. As a result, the process of analyzing the data becomes computationally complicated and time consuming. Spectral data often contains confounding spectral features that are frequently observed in microscopically acquired infrared spectra of cells and tissue, such as scattering and baseline artifacts. Thus, it is helpful to subject the spectral data to pre-processing to isolate the cellular material of interest, and to remove confounding spectral features.

One type of confounding spectral feature is Mie scattering, which is a sample morphology-dependent effect. This effect interferes with infrared absorption or reflection measurements if the sample is non-uniform and includes particles the size of approximately the wavelength of the light interrogating the sample. Mie scattering is manifested by broad, undulating scattering features, onto which the infrared absorption features are superimposed.

Mie scattering may also mediate the mixing of absorptive and reflective line shapes. In principle, pure absorptive line shapes are those corresponding to the frequency-dependence of the absorptivity, and are usually Gaussian, Lorentzian or mixtures of both. The absorption curves correspond to the imaginary part of the complex refractive index. Reflective contributions correspond to the real part of the complex refractive index, and are dispersive in line shapes. The dispersive contributions may be obtained from absorptive line shapes by numeric KK-transform, or as the real part of the complex Fourier transform (FT).

Resonance Mie (RMie) features result from the mixing of absorptive and reflective band shapes, which occurs because the refractive index undergoes anomalous dispersion when the absorptivity goes through a maximum (i.e., over the profile of an absorption band). Mie scattering, or any other optical effect that depends on the refractive index, will mix the reflective and absorptive line shapes, causing a distortion of the band profile, and an apparent frequency shift.

FIG. 1 illustrates the contamination of absorption patterns by dispersive band shapes observed in both SCP and SHP. The bottom trace in FIG. 1 depicts a regular absorption spectrum of biological tissue, whereas the top trace shows a spectrum strongly contaminated by a dispersive component via the RMie effect. The spectral distortions appear independent of the chemical composition, but rather depend on the morphology of the sample. The resulting band intensity and frequency shifts aggravate spectral analysis to the point that uncontaminated and contaminated spectra are classified into different groups due to the presence of the band shifts. Broad, undulating background features are shown in FIG. 2. When superimposed on the infrared micro-spectroscopy (IR-MSP) patterns of cells, these features are attributed to Mie scattering by spherical particles, such as cellular nuclei, or spherical cells.

The appearance of dispersive line shapes in FIG. 1 superimposed on IR-MSP spectra was reported along with a theoretical analysis in M. Romeo, et al., Vibrational Spectroscopy, 38, 129 (2005) (hereinafter "Romeo 2005"). Romeo 2005 indentifies the distorted band shapes as arising from the superposition of dispersive (reflective) components onto the absorption features of an infrared spectrum. These effects were attributed to incorrect phase correction of the instrument control software. In particular, the acquired raw interferogram in FTIR spectroscopy frequently is "chirped" or asymmetric, and needs to be symmetrized before FT. This is accomplished by collecting a double sided interferogram over a shorter interferometer stroke, and calculating a phase correction to yield a symmetric interferogram.

In Romeo 2005, it was assumed that this procedure was not functioning properly, which causes it to yield distorted spectral features. An attempt was made to correct the distorted spectral features by calculating the phase between the real and imaginary parts of the distorted spectra, and reconstructing a power spectrum from the phase corrected real and imaginary parts. Romeo 2005 also reported the fact that in each absorption band of an observed infrared spectrum, the refractive index undergoes anomalous dispersion. Under certain circumstances, various amounts of the dispersive line shapes can be superimposed, or mixed in, with the absorptive spectra.

The mathematical relationship between absorptive and reflective band shapes is given by the Kramers-Kronig (KK) transformation, which relates the two physical phenomena. The mixing of dispersive (reflective) and absorptive effects in the observed spectra was identified, and a method to correct the effect via a procedure called "Phase Correction" (PC) is discussed in Romeo 2005. Although the cause of the mixing of dispersive and absorptive contributions was erroneously attributed to instrument software malfunction, the principle of the confounding effect was properly identified. Due to the incomplete understanding of the underlying physics, however, the proposed correction method did not work properly.

P. Bassan et al., Analyst, 134, 1586 (2009) and P. Bassan et al., Analyst, 134, 1171 (2009) demonstrated that dispersive and absorptive effects may mix via the "Resonance Mie Scattering" (RMieS) effect. An algorithm and method to correct spectral distortion is described in P. Bassan et al., "Resonant Mie Scattering (RMieS) correction of infrared spectra from highly scattering biological samples", Analyst, 135, 268-277 (2010). This method is an extension of the "Extended Multiplicative Signal Correction" (EMSC) method reported in A. Kohler et al., Appl. Spectrosc., 59, 707 (2005) and A. Kohler et al., Appl. Spectrosc., 62, 259 (2008).

This method removes the non-resonant Mie scattering from infrared spectral datasets by including reflective components obtained via KK-transform of pure absorption spectra into a multiple linear regression model. The method utilizes the raw dataset and a "reference" spectrum as inputs, where the reference spectrum is used both to calculate the reflective contribution, and as a normalization feature in the EMSC scaling. Since the reference spectrum is not known a priori, Bassan et al. use the mean spectrum of the entire dataset, or an "artificial" spectrum, such as the spectrum of a pure protein matrix, as a "seed" reference spectrum. After the first pass through the algorithm, each corrected spectrum may be used in an iterative approach to correct all spectra in the subsequent pass. Thus, a dataset of 1000 spectra will produce 1000 RMieS-EMSC corrected spectra, each of which will be used as an independent new reference spectrum for the next pass, requiring 1,000,000 correction runs. To carry out this algorithm, referred to as the "RMieS-EMSC" algorithm, to a stable level of corrected output spectra required a number of passes (~10), and computation times that are measured in days.

Since the RMieS-EMSC algorithm requires hours or days of computation time, a fast, two-step method to perform the elimination of scattering and dispersive line shapes from spectra was developed, as discussed in B. Bird, M. Miljković and M. Diem, "Two step resonant Mie scattering correction of infrared micro-spectral data: human lymph node tissue", J. Biophotonics, 3 (8-9) 597-608 (2010). This approach includes fitting multiple dispersive components, obtained from KK-transform of pure absorption spectra, as well as Mie scattering curves computed via the van Hulst equation (see H. C. Van De Hulst, Light Scattering by Small Particles, Dover, Mineola, N. Y., (1981)), to all the spectra in a dataset via a procedure known as Extended Multiplicative Signal Correction (EMSC) (see A. Kohler et al., Appl. Spectrosc., 62, 259 (2008)) and reconstructing all spectra without these confounding components.

This algorithm avoids the iterative approach used in the RMieS-EMSC algorithm by using uncontaminated reference spectra from the dataset. These uncontaminated reference spectra were found by carrying out a preliminary cluster analysis of the dataset and selecting the spectra with the highest amide I frequencies in each cluster as the "uncontaminated" spectra. The spectra were converted to pure reflective spectra via numeric KK transform and used as interference spectra, along with compressed Mie curves for RMieS correction as described above. This approach is fast, but only works well for datasets containing a few spectral classes.

In the case of spectral datasets containing many tissue types, however, the extraction of uncontaminated spectra can become tedious. Furthermore, under these conditions, it is unclear whether fitting all spectra in the dataset to the most appropriate interference spectrum is guaranteed. In addition, this algorithm requires reference spectra for correction, and works best with large datasets.

In light of the above, there remains a need for improved methods of analyzing biological specimens by spectral imaging to provide a medical diagnosis. Further, there is a need for an improved pre-processing method that is based on a revised phase correction approach, does not require input data, is computationally fast, and takes into account many types of confounding spectral contributions that are frequently observed in microscopically acquired infrared spectra of cells and tissue.

SUMMARY

One aspect of the invention relates to a method for analyzing biological specimens by spectral imaging to provide a medical diagnosis. The method includes obtaining spectral and visual images of biological specimens and registering the images to detect abnormalities in the biological specimen, such as, but not limited to, cell abnormalities, pre-cancerous cells, and cancerous cells. This method overcomes the obstacles discussed above, among others, in that it eliminates the bias and unreliability of diagnoses and prognosis that are inherent in standard histopathological, cytological, and other spectral methods.

Another aspect of the invention relates to a method for correcting confounding spectral contributions that are frequently observed in microscopically acquired infrared spectra of cells and tissue by performing a phase correction on the spectral data. This phase correction method may be used to correct various kinds of absorption spectra that are contaminated by reflective components.

According to aspects of the invention, a method for analyzing biological specimens by spectral imaging includes acquiring a spectral image of the biological specimen, acquiring a visual image of the biological specimen, and registering the visual image and spectral image.

A method of developing a data repository according to aspects of the invention includes identifying a region of a visual image displaying a disease or condition, associating the region of the visual image to spectral data corresponding to the region, and storing the association between the spectral data and the corresponding disease or condition.

A method of providing a medical diagnosis according to aspects of the invention includes obtaining spectroscopic data for a biological specimen, comparing the spectroscopic data for the biological specimen to data in a repository that is associated with a disease or condition, determining any correlation between the repository data and the spectroscopic data for the biological specimen, and outputting a diagnosis associated with the determination.

A system for providing a medical diagnosis and prognosis, according to aspects of the invention includes a processor, a user interface functioning via the processor, and a repository accessible by the processor, where spectroscopic data of a biological specimen is obtained, the spectroscopic data for the biological specimen is compared to repository data that is associated with a disease or condition, any correlation between the repository data and the spectroscopic data for the biological specimen is determined; and a diagnosis associated with the determination is output.

A computer program product according to aspects of the invention includes a computer usable medium having control logic stored therein for causing a computer to provide a medical diagnosis. The control logic includes a first computer readable program code means for obtaining spectroscopic data for a biological specimen, second computer readable program code means for comparing the spectroscopic data for the biological specimen to repository data that is associated with a disease or condition, third computer readable program code means for determining any correlation between the repository data and the spectroscopic data for the biological specimen, and fourth computer readable program code means for outputting a diagnosis and/or or a prognostic determination associated with the determination.

DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2 shows broad, undulating background features typically observed on IR-MSP spectral of cells attributed to Mie scattering by spherical particles;

FIG. 3 is a flowchart illustrating a method of analyzing a biological sample by spectral imaging according to aspects of the invention;

FIG. 6A shows a typical spectrum, superimposed on a linear background according to aspects of the invention;

FIG. 6B shows an example of a second derivative spectrum according to aspects of the invention;

FIG. 11A shows the results of HCA after phase-correction using RMieS correction of FIG. 10D according to aspects of the invention;

FIG. 11B is H&E-based histopathology of the lymph node section of FIG. 11A according to aspects of the invention;

FIG. 13A is a visual microscopic image of a section of an H&E-stained axillary lymph node section according to aspects of the invention;

FIG. 13B is an infrared spectral image created from a Multilayer Perceptron Networks analysis of an infrared dataset collected prior to staining the tissue according to aspects of the invention;

FIG. 19C shows standard spectra for lung adenocarcinoma, small cell carcinoma, and squamous cell carcinoma according to aspects of the invention;

DETAILED DESCRIPTION

Figure 1:
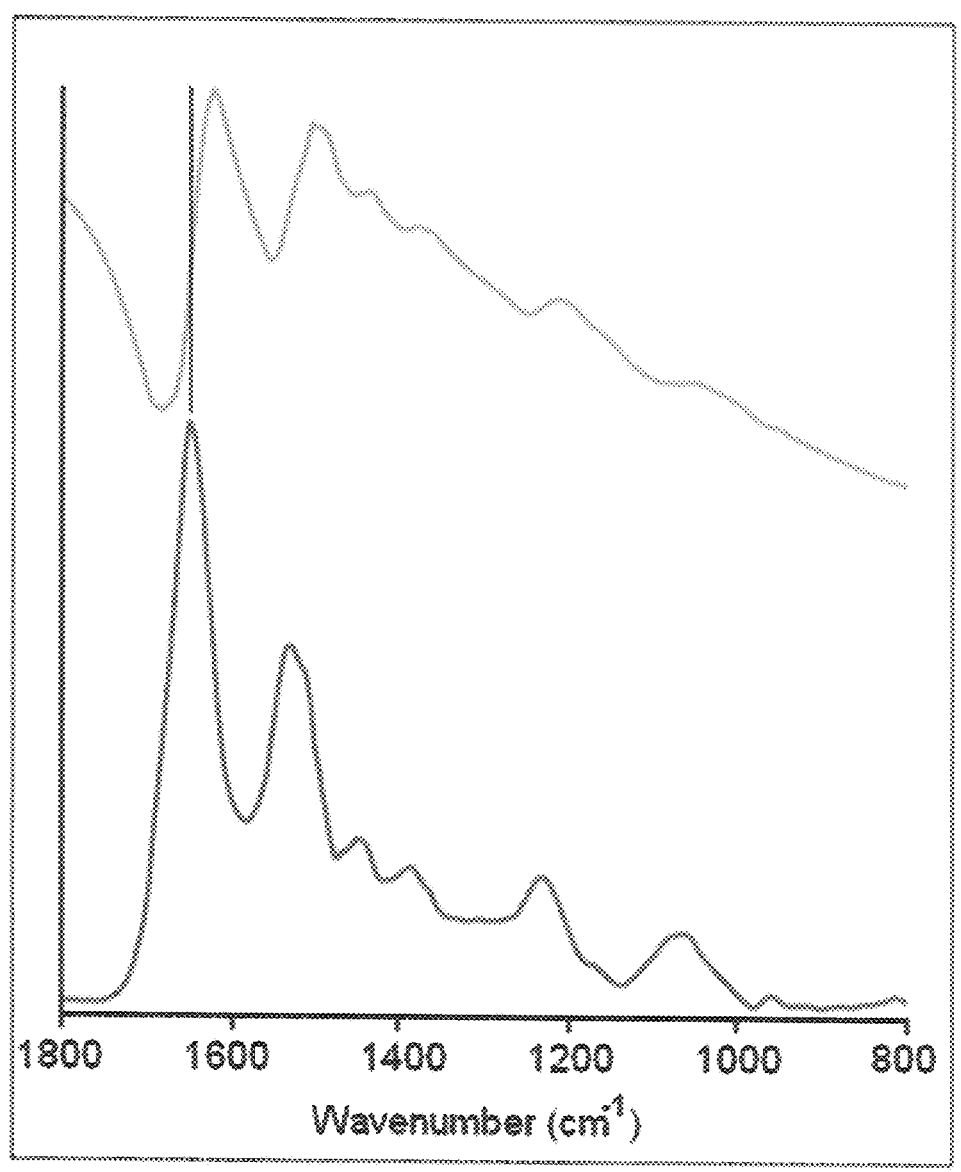
FIG. 1 illustrates the contamination of absorption patterns by dispersive band shapes typically observed in both SCP and SHP.

Unless otherwise defined, all technical and scientific terms used herein have the same meaning as commonly understood by one of ordinary skill in the art to which aspects of this invention belong. Although methods and materials similar or equivalent to those described herein can be used in the practice or testing, suitable methods and materials are described below. All publications, patent applications, patents, and other references mentioned herein are incorporated by reference in their entirety. In case of conflict, this specification, including definitions, will control. In addition, the materials, methods, and examples are illustrative only and not intended to be limiting.

One aspect of the invention relates to a method for analyzing biological specimens by spectral imaging to provide a medical diagnosis. The biological specimens may be medical specimens obtained by surgical methods, biopsies, and cultured samples. The method includes obtaining spectral and visual images of biological specimens and registering the images to detect cell abnormalities, pre-cancerous cells, and cancerous cells. The biological specimens may include tissue or cellular samples, but tissue samples are preferred for some applications. This method identifies abnormal or cancerous and other disorders including, but not limited to, lymph node, thyroid, breast, uterine, renal, testicular, ovarian, or prostate cancer, small cell lung carcinoma, non-small cell lung carcinoma, and melanoma, as well as non-cancerous effects including, but not limited to, inflammation, necrosis, and apoptosis.

One method in accordance with aspects of the invention overcomes the obstacles discussed above in that it eliminates or generally reduces the bias and unreliability of diagnoses, prognosis, predictive, and theranostics that are inherent in standard histopathological and other spectral methods. In addition, it allows access to a spectral database of tissue types that is produced by quantitative and reproducible measurements and is analyzed by an algorithm that is calibrated against classical histopathology. Via this method, for example, abnormal and cancerous cells may be detected earlier than they can be identified by the related art, including standard histopathological or other spectral techniques.

A method in accordance with aspects of the invention is illustrated in the flowchart of FIG. 3. As shown in FIG. 3, the method generally includes the steps of acquiring a biological section 301, acquiring a spectral image of the biological section 302, acquiring a visual image of the same biological section 303, and performing image registration 304. The registered image may optionally be subjected to training 305, and a medical diagnosis may be obtained 306.

Biological Section

According to the example method of the invention shown in FIG. 3, the step of acquiring a biological section 301 refers to the extraction of tissue or cellular material from an individual, such as a human or animal. A tissue section may be obtained by methods including, but not limited to core and punch biopsy, and excising. Cellular material may be obtained by methods including, but not limited to swabbing (exfoliation), washing (lavages), and by fine needle aspiration (FNA).

A tissue section that is to be subjected to spectral and visual image acquisition may be prepared from frozen or from paraffin embedded tissue blocks according to methods used in standard histopathology. The section may be mounted on a slide that may be used both for spectral data acquisition and visual pathology. For example, the tissue may be mounted either on infrared transparent microscope slides comprising a material including, but not limited to, calcium fluoride ($CaF_2$) or on infrared reflective slides, such as commercially available "low-e" slides. After mounting, paraffin-embedded samples may be subjected to deparaffinization.

Spectral Image

Figure 3A:
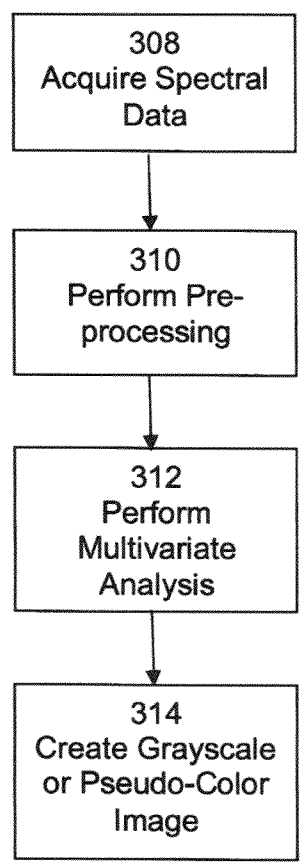
FIG. 3A is a flowchart illustrating steps in a method of acquiring a spectral image according to aspects of the invention.

According to aspects of the invention, the step of acquiring a spectral image of the biological section 302 shown in FIG. 3 may include acquiring spectral data from the biological section 308, performing data pre-processing 310, performing multivariate analysis 312, and creating a grayscale or pseudo-color image of the biological section 314, as outlined in the flowchart of FIG. 3A.

Spectral Data

As set forth in FIG. 3A, spectral data from the biological section may be acquired 401. Spectral data from an unstained biological sample, such as a tissue sample, may be obtained to capture a snapshot of the chemical composition of the sample. The spectral data may be collected from a tissue section in pixel detail, where each pixel is about the size of a cellular nucleus. Each pixel has its own spectral pattern, and when the spectral patterns from a sample are compared, they may show small but recurring differences in the tissue's biochemical composition.

The spectral data may be collected by methods including, but not limited to infrared, Raman, visible, terahertz, and fluorescence spectroscopy. Infrared spectroscopy may include, but is not limited to, attenuated total reflectance (ATR) and attenuated total reflectance Fourier transform infrared spectroscopy (ATR-FTIR). In general, infrared spectroscopy may be used because of its fingerprint sensitivity, which is also exhibited by Raman spectroscopy. Infrared spectroscopy may be used with larger tissue sections and to provide a dataset with a more manageable size than Raman spectroscopy. Furthermore, infrared spectroscopy data may be more amenable to fully automatic data acquisition and interpretation. Additionally, infrared spectroscopy may have the necessary sensitivity and specificity for the detection of various tissue structures and diagnosis of disease.

The intensity axis of the spectral data, in general, express absorbance, reflectance, emittance, scattering intensity or any other suitable measure of light power. The wavelength may relate to the actual wavelength, wavenumber, frequency or energy of electromagnetic radiation.

Infrared data acquisition may be carried out using presently available Fourier transform (FT) infrared imaging microspectrometers, tunable laser-based imaging instruments, such as quantum cascade or non-linear optical devices, or other functionally equivalent instruments based on different technologies. The acquisition of spectral data using a tunable laser is described further in U.S. patent application Ser. No. 13/084,287 titled, "Tunable Laser-Based Infrared Imaging System and Method of Use Thereof", which is incorporated herein in its entirety by reference.

According to one method in accordance with aspects of the invention, a pathologist or technician may select any region of a stained tissue section and receive a spectroscopy-based assessment of the tissue region in real-time, based on the hyperspectral dataset collected for the tissue before staining. Spectral data may be collected for each of the pixels in a selected unstained tissue sample. Each of the collected spectra contains a fingerprint of the chemical composition of each of the tissue pixels. Acquisition of spectral data is described in WO 2009/146425, which is incorporated herein in its entirety by reference.

In general, the spectral data includes hyperspectral datasets, which are constructs including $N=n \cdot m$ individual spectra or spectral vectors (absorption, emission, reflectance etc.), where n and m are the number of pixels in the x and y dimensions of the image, respectively. Each spectrum is associated with a distinct pixel of the sample, and can be located by its coordinates x and y, where $1 \leq x \leq n$, and $1 \leq y \leq m$. Each vector has k intensity data points, which are usually equally spaced in the frequency or wavenumber domain.

The pixel size of the spectral image may generally be selected to be smaller than the size of a typical cell so that subcellular resolution may be obtained. The size may also be determined by the diffraction limit of the light, which is typically about 5 μm to about 7 μm for infrared light. Thus, for a 1 $mm^2$ section of tissue, about $140^2$ to about $200^2$ individual pixel infrared spectra may be collected. For each of the N pixels of a spectral "hypercube", its x and y coordinates and its intensity vector (intensity vs. wavelength), are stored.

Pre-Processing

Subjecting the spectral data to a form of pre-processing may be helpful to isolate the data pertaining to the cellular material of interest and to remove confounding spectral features. Referring to FIG. 3A, once the spectral data is collected, it may be subjected to such pre-processing 310.

Pre-processing may involve creating a binary mask to separate diagnostic from non-diagnostic regions of the sampled area to isolate the cellular data of interest. Methods for creating a binary mask are disclosed in WO 2009/146425, which is incorporated by reference herein in its entirety.

A method of pre-processing, according to another aspect of the invention, permits the correction of dispersive line shapes in observed absorption spectra by a "phase correction" algorithm that optimizes the separation of real and imaginary parts of the spectrum by adjusting the phase angle between them. This method, which is computationally fast, is based on a revised phase correction approach, in which no input data are required. Although phase correction is used in the pre-processing of raw interferograms in FTIR and NMR spectroscopy (in the latter case, the interferogram is usually referred to as the "free induction decay, FID") where the proper phase angle can be determined experimentally, the method of this aspect of the invention differs from earlier phase correction approaches in that it takes into account mitigating factors, such as Mie, RMie and other effects based on the anomalous dispersion of the refractive index, and it may be applied to spectral datasets retroactively.

The pre-processing method of this aspect of the invention transforms corrupted spectra into Fourier space by reverse FT transform. The reverse FT results in a real and an imaginary interferogram. The second half of each interferogram is zero-filled and forward FT transformed individually. This process yields a real spectral part that exhibits the same dispersive band shapes obtained via numeric KK transform, and an imaginary part that includes the absorptive line shapes. By recombining the real and imaginary parts with a correct phase angle between them, phase-corrected, artifact-free spectra are obtained.

Since the phase required to correct the contaminated spectra cannot be determined experimentally and varies from spectrum to spectrum, phase angles are determined using a stepwise approach between −90° and 90° in user selectable steps. The "best" spectrum is determined by analysis of peak position and intensity criteria, both of which vary during phase correction. The broad undulating Mie scattering contributions are not explicitly corrected for explicitly in this approach, but they disappear by performing the phase correction computation on second derivative spectra, which exhibit a scatter-free background.

Figure 3B:
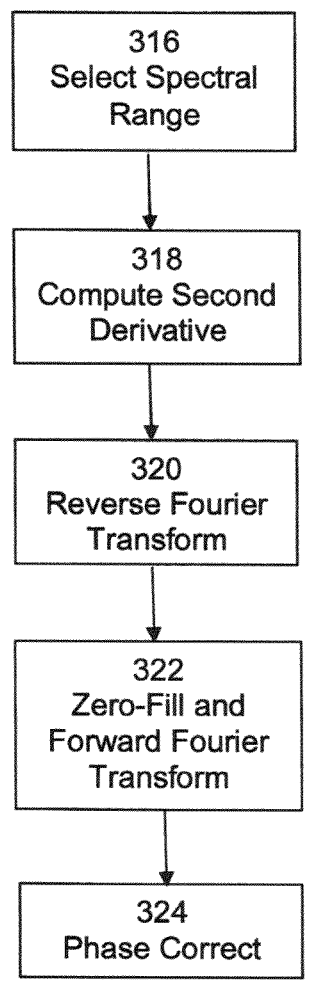
FIG. 3B is a flowchart illustrating steps in a method of pre-processing spectral data according to aspects of the invention.

According to aspects of the invention, pre-processing 310 as shown in FIG. 3A may include selecting the spectral range 316, computing the second derivative of the spectra 318, reverse Fourier transforming the data 320, zero-filling and forward Fourier transforming the interferograms 322, and phase correcting the resulting real and imaginary parts of the spectrum 324, as outlined in the flowchart of FIG. 3B.

Spectral Range

In 316, each spectrum in the hyperspectral dataset is pre-processed to select the most appropriate spectral range (fingerprint region). This range may be about 800 to about 1800 $cm^{-1}$, for example, which includes heavy atom stretching as well as X-H (X: heavy atom with atomic number $\geq 12$) deformation modes. A typical example spectrum, superimposed on a linear background, is shown in FIG. 6A.

Second Derivative of Spectra

The second derivative of each spectrum is then computed 318 as shown in the flowchart of FIG. 3B. Second derivative spectra are derived from original spectral vectors by second differentiation of intensity vs. wavenumber. Second derivative spectra may be computed using a Savitzky-Golay sliding window algorithm, and can also be computed in Fourier space by multiplying the interferogram by an appropriately truncated quadratic function.

Second derivative spectra may have the advantage of being free of baseline slopes, including the slowly changing Mie scattering background. The second derivative spectra may be nearly completely devoid of baseline effects due to scattering and non-resonant Mie scattering, but still contain the effects of RMieS. The second derivative spectra may be vector normalized, if desired, to compensate for varying sample thickness. An example of a second derivative spectrum is shown in FIG. 6B.

Reverse Fourier Transform

Figure 7:
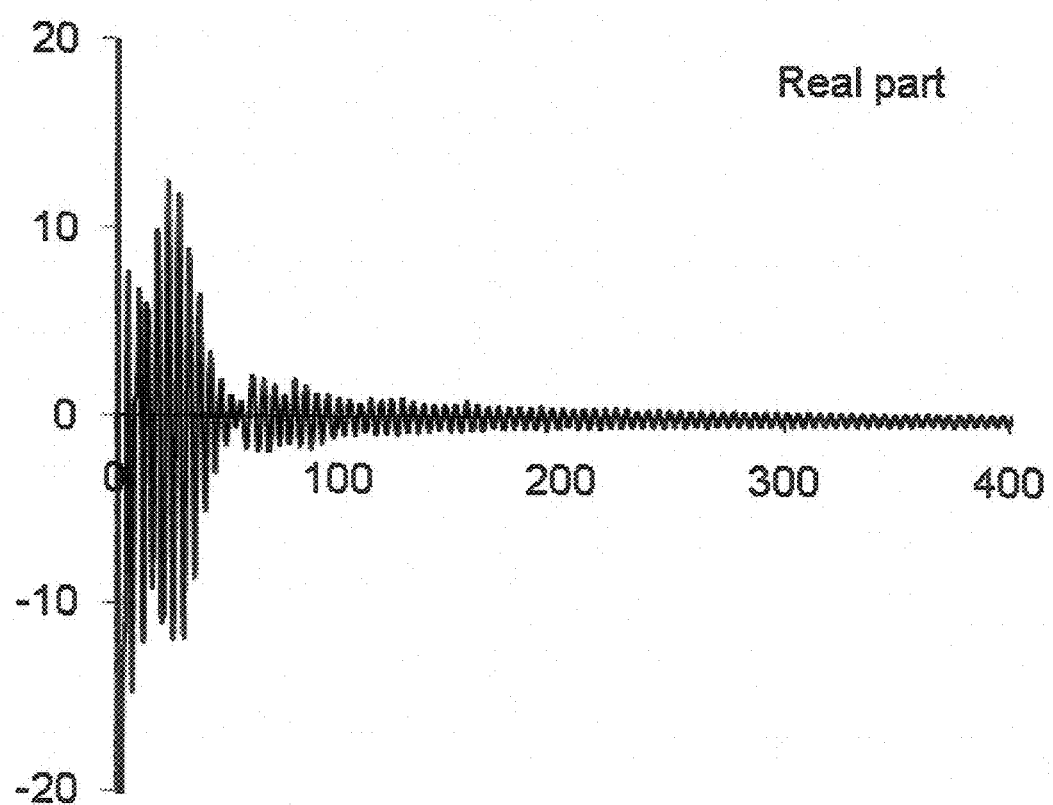
FIG. 7 shows a portion of the real part of an interferogram according to aspects of the invention.

As shown in 320 of the flowchart of FIG. 3B, each spectrum of the data set is reverse Fourier transformed (FT). Reverse FT refers to the conversion of a spectrum from intensity vs. wavenumber domain to intensity vs. phase difference domain. Since FT routines only work with spectral vectors the length of which are an integer power of 2, spectra are interpolated or truncated to 512, 1024 or 2048 (NFT) data point length before FT. Reverse FT yields a real (RE) and imaginary (IM) interferogram of NFT/2 points. A portion of the real part of such an interferogram is shown in FIG. 7.

Zero-Fill and Forward Fourier Transform

The second half of both the real and imaginary interferogram for each spectrum is subsequently zero-filled 322. These zero-filled interferograms are subsequently forward Fourier transformed to yield a real and an imaginary spectral component with dispersive and absorptive band shapes, respectively.

Phase Correction

The real (RE) and imaginary (IM) parts resulting from the Fourier analysis are subsequently phase corrected 324, as shown in the flowchart of FIG. 3B. This yields phase shifted real (RE') and imaginary (IM') parts as set forth in the formula below:

$$\begin{pmatrix} RE' \\ IM' \end{pmatrix} = \begin{pmatrix} \cos(\phi) & \sin(\phi) \\ -\sin(\phi) & \cos(\phi) \end{pmatrix} \begin{pmatrix} RE \\ IM \end{pmatrix},$$

where $\phi$ is the phase angle.

Figure 8:
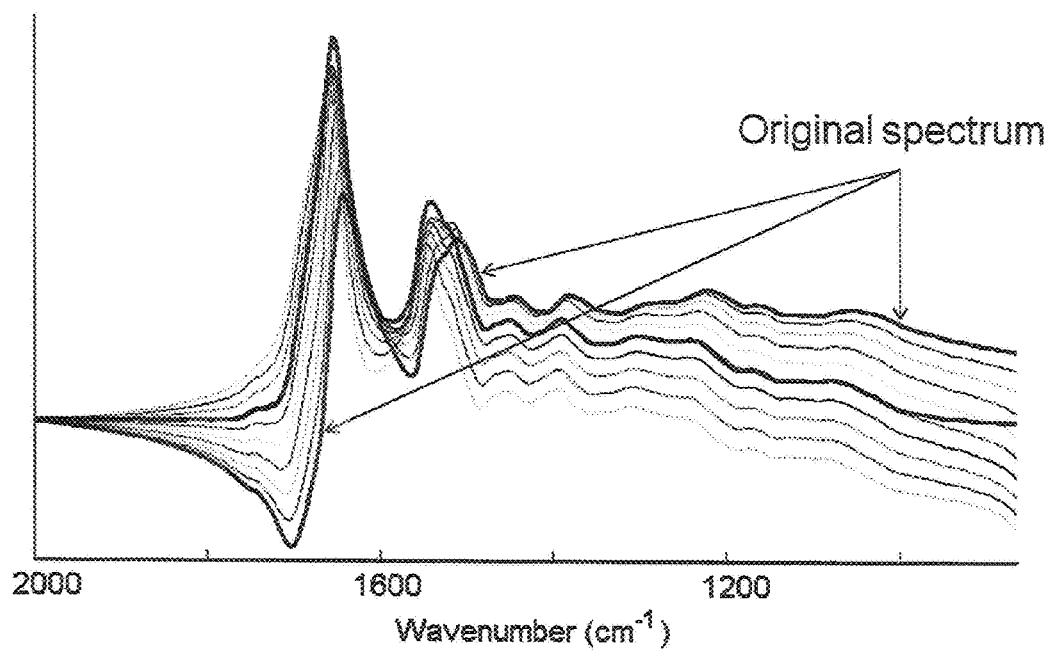
FIG. 8 shows that the phase angle that produces the largest intensity after phase correction is assumed to be the uncorrupted spectrum according to aspects of the invention.

Since the phase angle $\phi$ for the phase correction is not known, the phase angle may be varied between $-\pi/2 \leq \phi \leq \pi/2$ in user defined increments, and a spectrum with the least residual dispersive line shape may be selected. The phase angle that produces the largest intensity after phase correction may be assumed to be the uncorrupted spectrum, as shown in FIG. 8. The heavy trace marked with the arrows and referred to as the "original spectrum" is a spectrum that is contaminated by RMieS contributions. The thin traces show how the spectrum changes upon phase correction with various phase angles. The second heavy trace is the recovered spectrum, which matches the uncontaminated spectrum well. As indicated in FIG. 8, the best corrected spectrum exhibits the highest amide I intensity at about 1655 cm$^{-1}$. This peak position matches the position before the spectrum was contaminated.

Figure 9A:
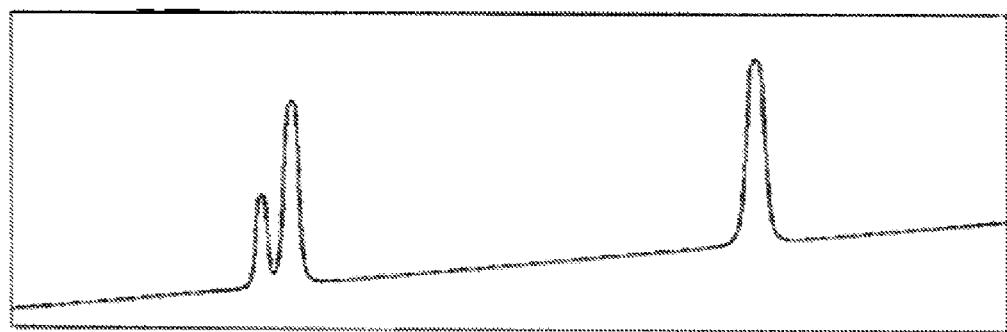
FIG. 9A shows that absorption spectra that are contaminated by scattering effects that mimic a baseline slope according to aspects of the invention.
Figure 9B:
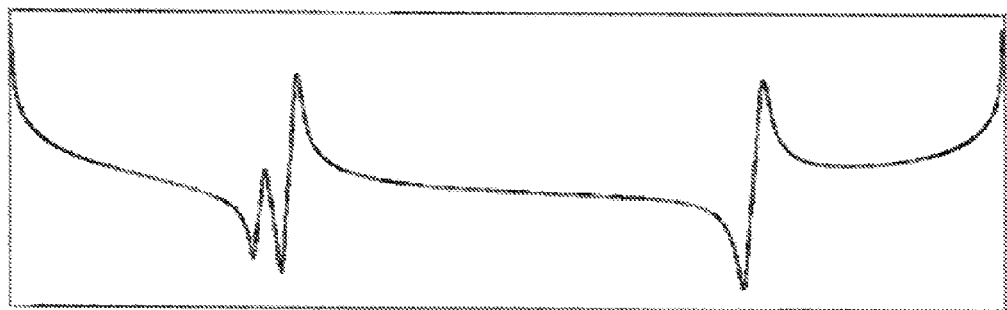
FIG. 9B shows that the imaginary part of the forward FT exhibits strongly curved effects at the spectral boundaries, which will contaminate the resulting corrected spectra according to aspects of the invention.

The phase correction method, in accordance with aspects of the invention in 316-324, works well both with absorption and derivative spectra. This approach even solves a complication that may occur if absorption spectra are used, in that if absorption spectra are contaminated by scattering effects that mimic a baseline slope, as shown schematically in FIG. 9A, the imaginary part of the forward FT exhibits strongly curved effects at the spectral boundaries, as shown in FIG. 9B, which will contaminate the resulting corrected spectra. Use of second derivative spectra may eliminate this effect, since the derivation eliminates the sloping background; thus, artifact-free spectra may be obtained. Since the ensuing analysis of the spectral data-set by hierarchical cluster analysis, or other appropriate segmenting or diagnostic algorithms, is carried out on second derivative spectra anyway, it is advantageous to carry out the dispersive correction on second derivative spectra, as well. Second derivative spectra exhibit reversal of the sign of spectral peaks. Thus, the phase angle is sought that causes the largest negative intensity. The value of this approach may be demonstrated from artificially contaminated spectra: since a contamination with a reflective component will always decrease its intensity, the uncontaminated or "corrected" spectrum will be the one with the largest (negative) band intensity in the amide I band between 1650 and 1660 cm$^{-1}$.

Example 1

Operation of Phase Correction Algorithm

An example of the operation of the phase correction algorithm is provided in FIGS. 10 and 11. This example is based on a dataset collected from a human lymph node tissue section. The lymph node has confirmed breast cancer micrometastases under the capsule, shown by the black arrows in FIG. 10A. This photo-micrograph shows distinct cellular nuclei in the cancerous region, as well as high cellularity in areas of activated lymphocytes, shown by the gray arrow. Both these sample heterogeneities contribute to large RMieS effects.

Figure 10A:
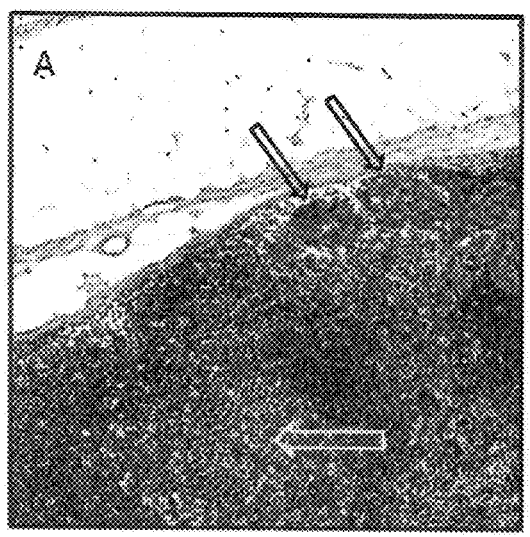
FIG. 10A is H&E-based histopathology showing a lymph node that has confirmed breast cancer micro-metastases under the capsule according to aspects of the invention.
Figure 10B:
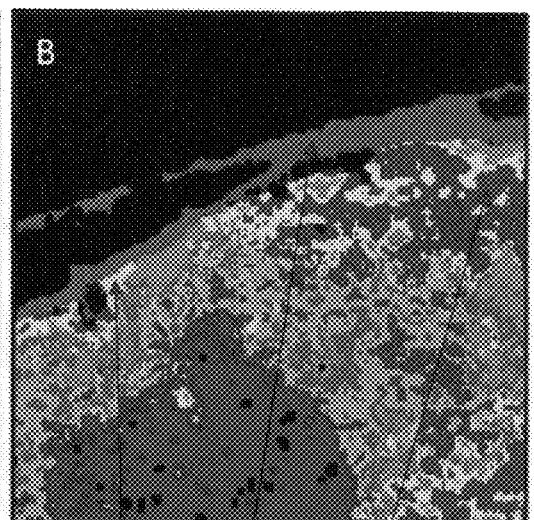
FIG. 10B shows data segmentation by Hierarchical Cluster Analysis (HCA) carried out on the lymph node section of FIG. 10A according to aspects of the invention.

When data segmentation by hierarchical cluster analysis (HCA) was first carried out on this example lymph node section, the image shown in FIG. 10B was obtained. To distinguish the cancerous tissue (dark green and yellow) from the capsule (red), and the lymphocytes (remainder of colors), 10 clusters were necessary, and the distinction of these tissue types was poor. In FIG. 10B, the capsule shown in red includes more than one spectral class, which were combined into 1 cluster.

Figure 10C:
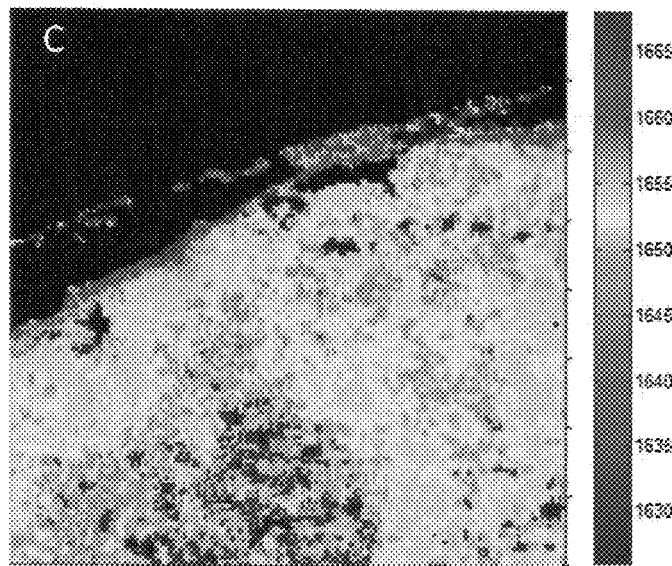
FIG. 10C is a plot showing the peak frequencies of the amide I vibrational band in each spectrum according to aspects of the invention.
Figure 10D:
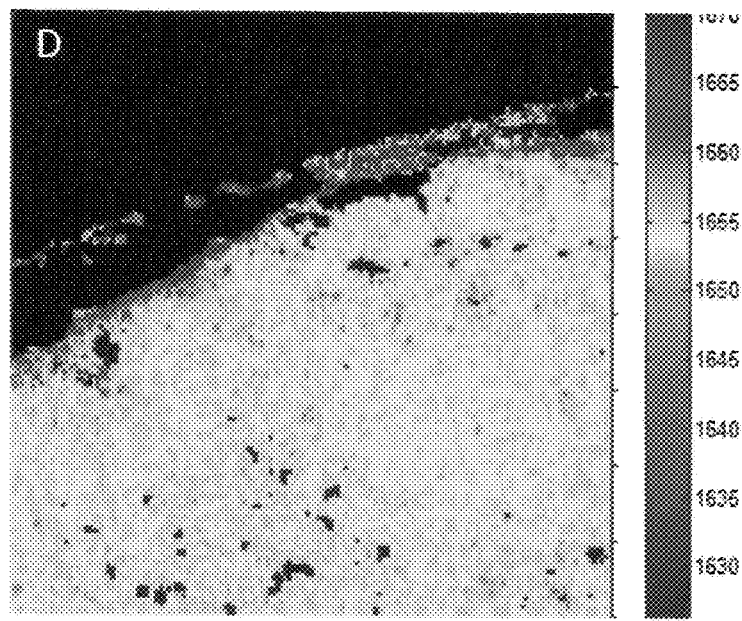
FIG. 10D shows an image of the same lymph node section of FIG. 10A after phase-correction using RMieS correction according to aspects of the invention.

The difficulties in segmenting this dataset can be gauged by inspection of FIG. 10C. This plot depicts the peak frequencies of the amide I vibrational band in each spectrum. The color scale at right of the figure indicates that the peak occurs between about 1630 and 1665 cm$^{-1}$ of the lymph node body, and between 1635 and 1665 cm$^{-1}$ for the capsule. The spread of amide I frequency is typical for a dataset heavily contaminated by RMieS effects, since it is well-known that the amide I frequency for peptides and proteins should occur in the range from 1650 to 1660 cm$^{-1}$, depending on the secondary protein structure. FIG. 10D shows an image of the same tissue section after phase-correction based RMieS correction. Within the body of the lymph node, the frequency variation of the amide I peak was reduced to the range of 1650 to 1654 cm$^{-1}$, and for the capsule to a range of 1657 to 1665 cm$^{-1}$ (fibro-connective proteins of the capsule are known to consist mostly of collagen, a protein known to exhibit a high amide I band position).

The results from a subsequent HCA are shown in FIG. 11. In FIG. 11A, cancerous tissue is shown in red; the outline of the cancerous regions coincides well with the H&E-based histopathology shown in FIG. 11B (this figure is the same as 10A). The capsule is represented by two different tissue classes (light blue and purple), with activated B-lymphocytes shown in light green. Histiocytes and T-lymphocytes are shown in dark green, gray and blue regions. The regions depicted in FIG. 11A match the visual histopathology well, and indicate that the phase correction method discussed herein improved the quality of the spectral histopathology methods enormously. In an aspect, narrow band normalization may also be used to enhance and/or improve the quality of the image, which may be helpful for image registration accuracy. The narrow band normalization may select features and/or subsets of features within the broad band spectral region and apply a weighting to the selected features.

The advantages of the pre-processing method in accordance with aspects of the invention over previous methods of spectral correction include that the method provides a fast execution time of about 5000 spectra/second, and no a priori information on the dataset is required. In addition, the phase correction algorithm can be incorporated into spectral imaging and "digital staining" diagnostic routines for automatic cancer detection and diagnosis in SCP and SHP. Further, phase correction greatly improves the quality of the image, which is helpful for image registration accuracy and in diagnostic alignment and boundary representations.

Further, the pre-processing method in accordance with aspects of the invention may be used to correct a wide range of absorption spectra contaminated by reflective components. Such contamination occurs frequently in other types of spectroscopy, such as those in which band shapes are distorted by dispersive line shapes, such as Diffuse Reflectance Fourier Transform Spectroscopy (DRIFTS), Attenuated Total Reflection (ATR), and other forms of spectroscopy in which mixing of the real and imaginary part of the complex refractive index, or dielectric susceptibility, occurs to a significant extent, such as may be present with Coherent Anti-Stokes Raman Spectroscopy (CARS).

Multivariate Analysis

Multivariate analysis may be performed on the pre-processed spectral data to detect spectral differences, as outlined in 312 of the flowchart of FIG. 3A. In certain multivariate analyses, spectra are grouped together based on similarity. The number of groups may be selected based on the level of differentiation required for the given biological sample. In general, the larger the number of groups, the more detail that will be evident in the spectral image. A smaller number of groups may be used if less detail is desired. According to aspects of the invention, a user may adjust the number of groups to attain the desired level of spectral differentiation.

For example, unsupervised methods, such as HCA and principal component analysis (PCA), supervised methods, such as machine learning algorithms including, but not limited to, artificial neural networks (ANNs), hierarchical artificial neural networks (hANN), support vector machines (SVM), and/or "random forest" algorithms may be used. Unsupervised methods are based on the similarity or variance in the dataset, respectively, and segment or cluster a dataset by these criteria, requiring no information except the dataset for the segmentation or clustering. Thus, these unsupervised methods create images that are based on the natural similarity or dissimilarity (variance) in the dataset. Supervised algorithms, on the other hand, require reference spectra, such as representative spectra of cancer, muscle, or bone, for example, and classify a dataset based on certain similarity criteria to these reference spectra.

HCA techniques are disclosed in Bird (Bird et al., "Spectral detection of micro-metastates in lymph node histopathology", J. Biophoton. 2, No. 1-2, 37-46 (2009)), which is incorporated herein in its entirety. PCA is disclosed in WO 2009/146425, which is incorporated by reference herein in its entirety.

Examples of supervised methods for use in accordance with aspects of the invention may be found in P. Lasch et al. "Artificial neural networks as supervised techniques for FT-IR microspectroscopic imaging" J. Chemometrics 2006 (hereinafter "Lasch"); 20: 209-220, M. Miljkovic et al., "Label-free imaging of human cells: algorithms for image reconstruction of Raman hyperspectral datasets" (hereinafter "Miljkovic"), Analyst, 2010, xx, 1-13, and A. Dupuy et al., "Critical Review of Published Microarray Studies for Cancer Outcome and Guidelines on Statistical Analysis and Reporting", JNCI, Vol. 99, Issue 2|Jan. 17, 2007 (hereinafter "Dupuy"), each of which is incorporated by reference herein in its entirety.

Grayscale or Pseudo-Color Spectral Image

Similarly grouped data from the multivariate analysis may be assigned the same color code. The grouped data may be used to construct "digitally stained" grayscale or pseudo-color maps, as set forth in 314 of the flowchart of FIG. 3A. Accordingly, this method may provide an image of a biological sample that is based solely or primarily on the chemical information contained in the spectral data.

Figure 12A:
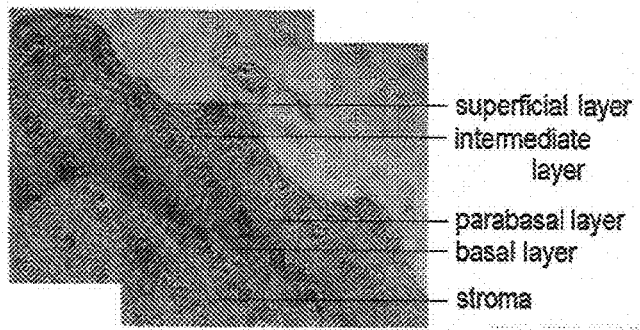
FIG. 12A is a visual microscopic image of a section of stained cervical image.
Figure 12B:
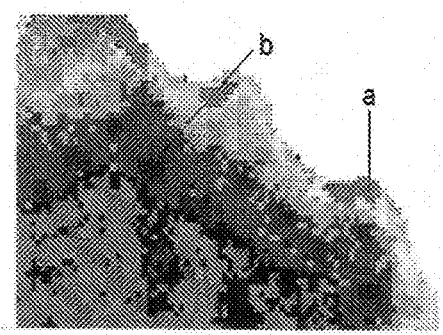
FIG. 12B is an infrared spectral image created from hierarchical cluster analysis of an infrared dataset collected prior to staining the tissue according to aspects of the invention.

An example of a spectral image prepared after multivariate analysis by HCA is provided in FIGS. 12A and 12B. FIG. 12A is a visual microscopic image of a section of stained cervical image, measuring about 0.5 mm×1 mm. Typical layers of squamous epithelium are indicated. FIG. 12B is a pseudo-color infrared spectral image constructed after multivariate analysis by HCA prior to staining the tissue. This image was created by mathematically correlating spectra in the dataset with each other, and is based solely on spectral similarities; no reference spectra were provided to the computer algorithm. As shown in FIG. 12B, an HCA spectral image may reproduce the tissue architecture visible after suitable staining (for example, with a H&E stain) using standard microscopy, as shown in FIG. 12A. In addition, FIG. 12B shows features that are not readily detected in FIG. 12A, including deposits of keratin at (a) and infiltration by immune cells at (b).

The construction of pseudo-color spectral images by HCA analysis is discussed in Bird.

An example of a spectral image prepared after analysis by ANN is provided in FIGS. 13A and 13B. FIG. 13A is a visual microscopic image of a section of an H&E-stained axillary lymph node section. FIG. 13B is an infrared spectral image created from ANN analysis of an infrared dataset collected prior to staining the tissue of FIG. 13A.

Visual Image

A visual image of the same biological section obtained in 302 may be acquired, as indicated by 303 as shown in FIG. 3. The biological sample applied to a slide in step 301 described above may be unstained or may be stained by any suitable well-known method used in standard histopathology, such as by one or more H&E and/or IHC stains, and may be coverslipped. Examples of visual images are shown in FIGS. 12A and 13A.

A visual image of a histopathological sample may be obtained using a standard visual microscope, such as one commonly used in pathology laboratories. The microscope may be coupled to a high resolution digital camera that captures the field of view of the microscope digitally. This digital real-time image is based on the standard microscopic view of a stained piece of tissue, and is indicative of tissue architecture, cell morphology and staining patterns. The digital image may include many pixel tiles that are combined via image stitching, for example, to create a photograph. According to aspects of the invention, the digital image that is used for analysis may include an individual tile or many tiles that are stitched combined into a photograph. This digital image may be saved and displayed on a computer screen.

Registration of Spectral and Visual Images

According to one method in accordance with aspects of the invention, once the spectral and visual images have been acquired, the visual image of the stained tissue may be registered with a digitally stained grayscale or pseudo-color spectral image, as indicated in 304 of the flowchart of FIG.

3. In general, image registration is the process of transforming or matching different sets of data into one coordinate system. Image registration involves spatially matching or transforming a first image to align with a second image. The pixels in the first image and the pixels in the second image may coincide to the same points in the coordinate system. The images may contain different types of data, and image registration allows the matching or transformation of the different types of data. In an aspect, the transformation may include a scaled rigid body transformation. It should be noted that the transformation may include warping if staining the sample made the sample shrink non-uniformly. Example transformation equations that the computing system may use include the following:

$$u = u0 + scale*(x*\cos(\theta) - y*\sin(\theta))$$

$$v = v0 + scale*(x*\sin(\theta) + y*\cos(\theta))$$

where (u0,v0) is a shift of the origin, θ is a rotation angle in radians and scale is the scale factor, (x,y) are coordinates in the HCA image, and (u,v) are coordinates in the H&E (visual image).

In accordance with aspects of the invention, image registration may be performed in a number of ways. For example, a common coordinate system may be established for the visual and spectral images. If establishing a common coordinate system is not possible or is not desired, the images may be registered by point mapping to bring an image into alignment with another image. In point mapping, control points on both of the images that identify the same feature or landmark in the images are selected. Based on the positions of the control points, spatial mapping of both images may be performed. For example, at least two control points may be used. To register the images, the control points in the visible image may be correlated to the corresponding control points in the spectral image and aligned together.

In an aspect, at least two control points may be used to determine the transformation parameters of the scaled body transformation. The transformation parameters may be selected to minimize an error between the mapped control points in the registered images (e.g., the overlapped images). For example, when two control points are used to determine the transformation parameters, two solutions for the transformation may be generated by the computing system. The computing system may select one of the two solutions generated based upon, for example, the orientation of the image. However, when three control points are used to determine the transformation parameters, a unique solution for the transformation may be generated by the computing system. Thus, it should be noted that more than two control points may be used by the computing system to determine the parameters of the scaled body transformation. In addition, as the number of control points increase, the accuracy of the transformation may also increase and/or improve.

In one variation according to aspects of the invention, control points may be selected by placing reference marks on the slide containing the biological specimen. Reference marks may include, but are not limited to, ink, paint, and a piece of a material, including, but not limited to polyethylene. The reference marks may have any suitable shape or size, and may be placed in the central portion, edges, or corners of the side, as long as they are within the field of view. The reference mark may be added to the slide while the biological specimen is being prepared. If a material having known spectral patterns, including, but not limited to a chemical substance, such as polyethylene, and a biological substance, is used in a reference mark, it may be also used as a calibration mark to verify the accuracy of the spectral data of the biological specimen.

In another variation according to aspects of the invention, a user, such as a pathologist, may select the control points in the spectral and visual images. The user may select the control points based on their knowledge of distinguishing features of the visual or spectral images including, but not limited to, edges and boundaries. For biological images such as cells and tissue, control points may be selected from any of the biological features in the image. For example, such biological features may include, but are not limited to, clumps of cells, mitotic features, cords or nests of cells, sample voids, such as alveolar and bronchi, and irregular sample edges. The user's selection of control points in the spectral and visual images may be saved to a repository that is used to provide a training correlation for personal and/or customized use. This approach may allow subjective best practices to be incorporated into the control point selection process.

In another variation according to aspects of the invention, software-based recognition of distinguishing features in the spectral and visual images may be used to select control points. The software may detect at least one control point that corresponds to a distinguishing feature in the visual or spectral images. For example, control points in a particular a cluster region may be selected in the spectral image. The cluster pattern may be used to identify similar features in the visual image. The control points may be used to digitally correlate the pixels from the spectral image with the pixels from the visual image. In another aspect, the software may use morphological (e.g., shape) features in the images to select the control points. The morphological features may come from the shape of the specimen, the shape of the spaces between the tissues, and/or the shape of stained regions within the tissue (e.g., as a result of staining the biological sample, for example, with an IHC agent). Thus, any shape that may occur in the visual image that also occurs in the spectral image may be used to select the control points.

The features in both images may be aligned by translation, rotation, and scaling. Translation, rotation and scaling may also be automated or semi-automated, for example, by developing mapping relationships or models after selecting the features selection. Such an automated process may provide an approximation of mapping relationships that may then be resampled and transformed to optimize registration, for example. Resampling techniques include, but are not limited to nearest neighbor, linear, and cubic interpolation.

Once the control points are aligned, the pixels in the spectral image having coordinates $P_1$ ($x_1$, $y_1$) may be aligned with the corresponding pixels in the visual image having coordinates $P_2$ ($x_2$, $y_2$). This alignment process may be applied to all or a selected portion of the pixels in the spectral and visual images. Once aligned, the pixels in each of the spectral and visual images may be registered together. By this registration process, the pixels in each of the spectral image and visual images may be digitally joined with the pixels in the corresponding image. Since the method in accordance with aspects of the invention allows the same biological sample to be tested spectroscopically and visually, the visual and spectral images may be registered accurately.

An identification mark such as a numerical code, bar code, may be added to the slide to verify that the correct specimen is being accessed. The reference and identification marks may be recognized by a computer that displays or otherwise stores the visual image of the biological specimen. This computer may also contain software for use in image registration.

Figure 14A:
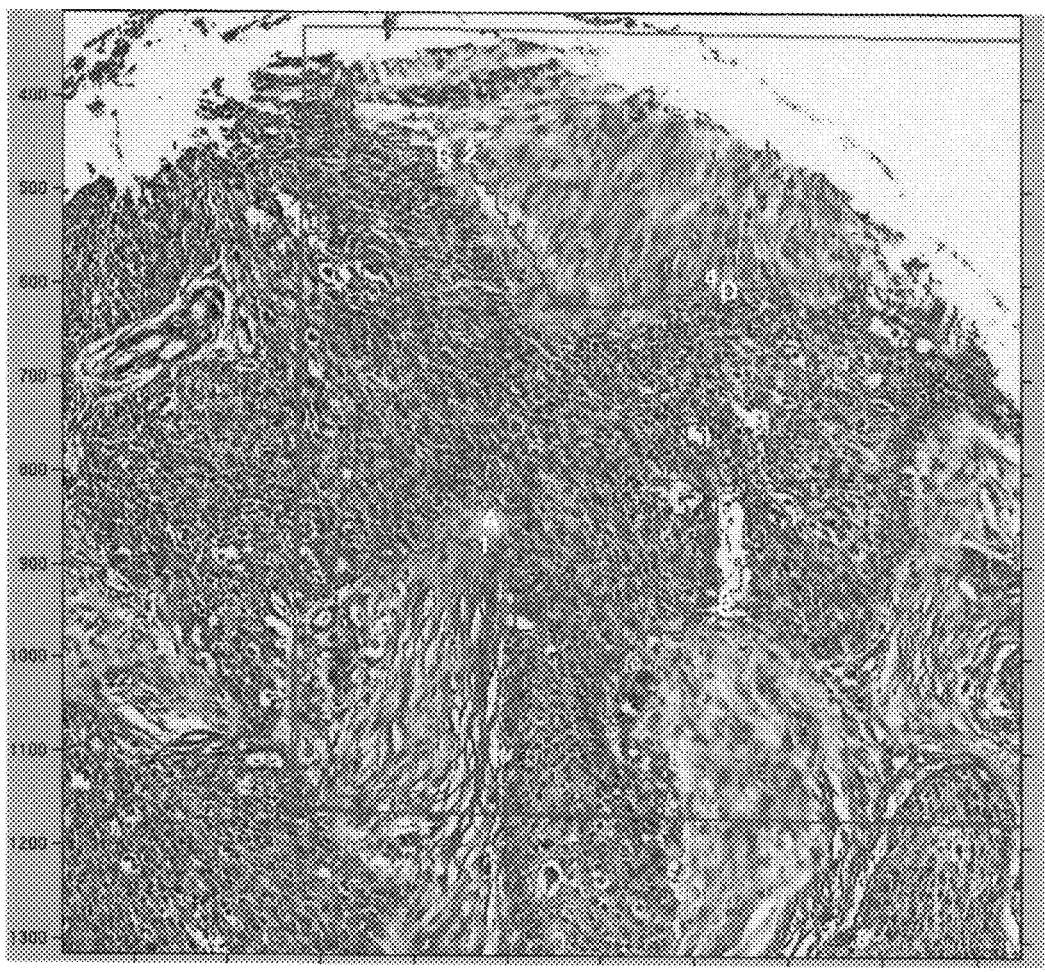
FIG. 14A is a visual image of a small cell lung cancer tissue according to aspects of the invention.
Figure 14B:
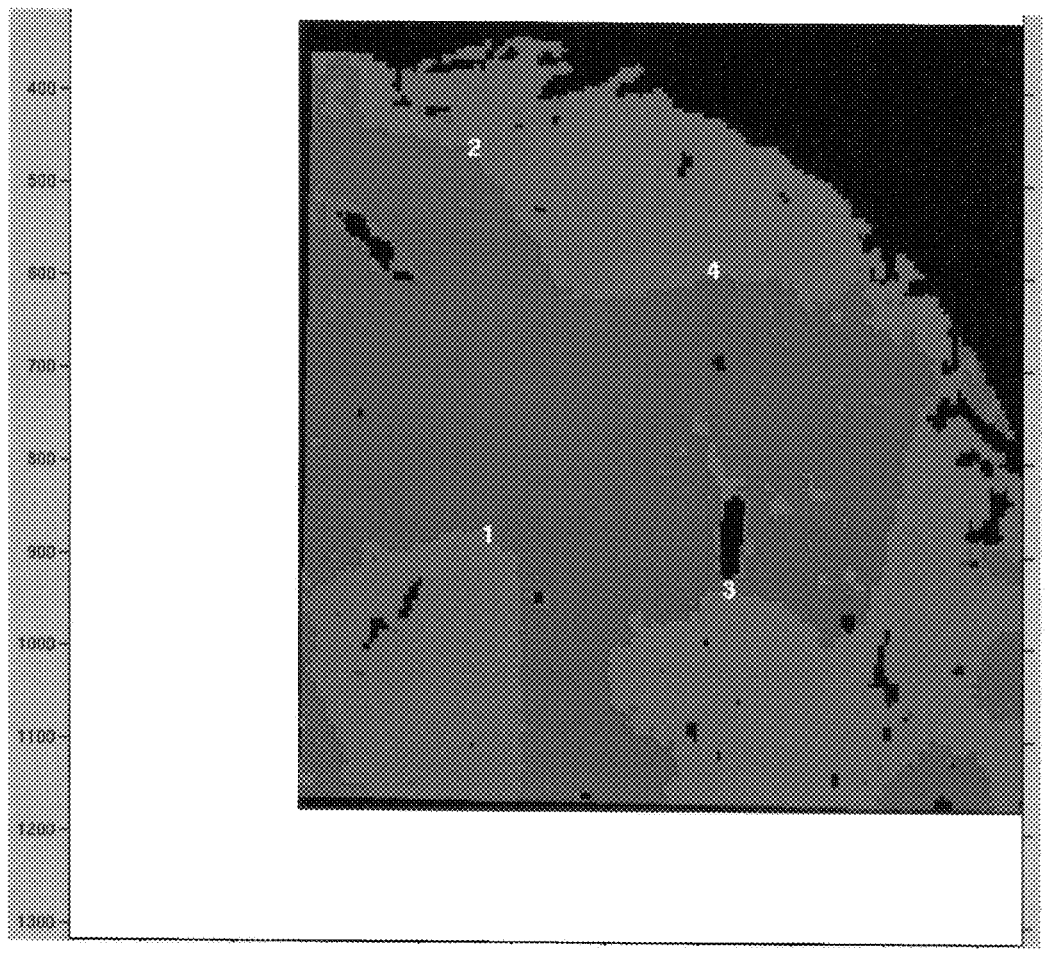
FIG. 14B is an HCA-based spectral image of the tissue shown in FIG. 14A according to aspects of the invention.
Figure 14C:
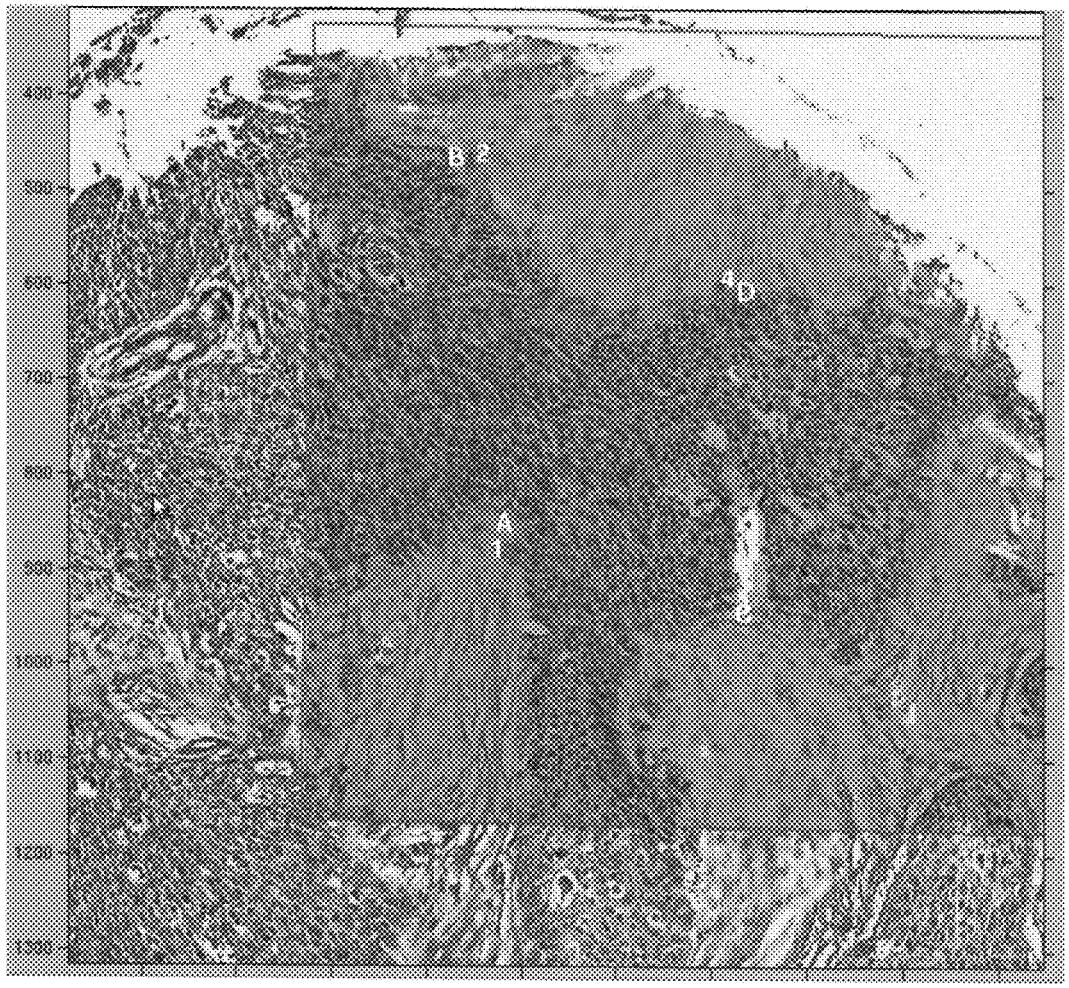
FIG. 14C is a registered image of the visual image of FIG. 14A and the spectral image of FIG. 14B, according to aspects of the invention.

An example of image registration according to an aspect of the invention is illustrated in FIGS. 14A-14C. FIG. 14A is a visual image of a small cell lung cancer tissue sample, and FIG. 14B is spectral image of the same tissue sample subjected to HCA. FIG. 14B contains spectral data from most of the upper right-hand section of the visual image of FIG. 14A. When the visual image of FIG. 14A is registered with the spectral image of FIG. 14B, the result is shown in FIG. 14C. As shown in FIG. 14C, the circled sections containing spots and contours 1-4 that are easily viewable in the spectral image of FIG. 14B correspond closely to the spots and contours visible in the microscopic image of FIG. 14A.

Once the coordinates of the pixels in the spectral and visual images are registered, they may be digitally stored together. The entire images or a portion of the images may be stored. For example, the diagnostic regions may be digitally stored instead of the images of the entire sample. This may significantly reduce data storage requirements.

Figure 14D:
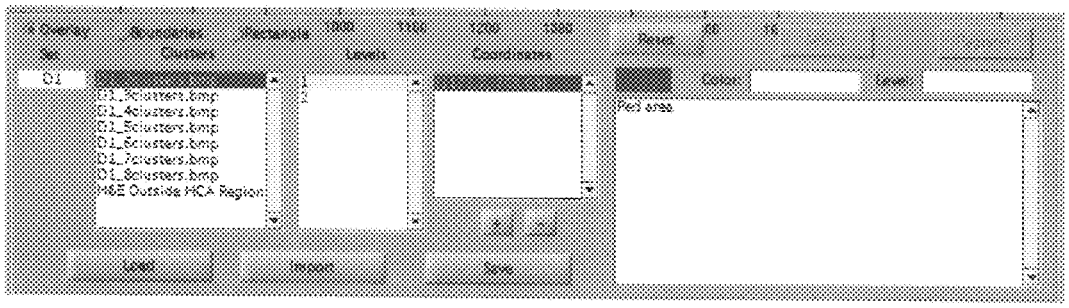
FIG. 14D is an example of a graphical user interface (GUI) for the registered image of FIG. 14C according to aspects of the invention.

A user who views a certain pixel region in either the spectral or visual image may immediately access the corresponding pixel region in the other image. For example, a pathologist may select any area of the spectral image, such as by clicking a mouse or with joystick control, and view the corresponding area of the visual image that is registered with the spectral image. FIG. 14D is an example of a graphical user interface (GUI) for the registered image of FIG. 14C according to aspects of the invention. The GUI shown in FIG. 14D allows a pathologist to toggle between the visual, spectral, and registered images and examine specific portions of interest.

In addition, as a pathologist moves or manipulates an image, he/she can also access the corresponding portion of the other image to which it is registered. For example, if a pathologist magnifies a specific portion of the spectral image, he/she may access the same portion in the visual image at the same level of magnification.

Operational parameters of the visual microscope system, as well as microscope magnification, changes in magnification etc., may be also stored in an instrument specific log file. The log file may be accessed at a later time to select annotation records and corresponding spectral pixels for training the algorithm. Thus, a pathologist may manipulate the spectral image, and at a later time, the spectral image and the digital image that is registered to it are both displayed at the appropriate magnification. This feature may be useful, for example, since it allows a user to save a manipulated registered image digitally for later viewing or for electronic transmittal for remote viewing.

Image registration may be used with a tissue section, a cell section, and/or any other biological sample having a known diagnosis, prognosis, and/or predictive use to extract training spectra during a training step of a method in accordance with aspects of the invention. During the training step, a visual image of stained tissue may be registered with an unsupervised spectral image, such as from HCA. Image registration may also be used when making a diagnosis, prognosis, and/or predictive use on a tissue section. For example, a supervised spectral image of the tissue section may be registered with its corresponding visual image. Thus, a user may obtain a diagnosis, prognosis, and/or predictive use based on any point in the registered images that has been selected.

Image registration according to aspects of the invention provides numerous advantages over prior methods of analyzing biological samples. For example, it allows a pathologist to rely on a spectral image, which reflects the highly sensitive biochemical content of a biological sample, when making analyzing biological material. As such, it provides significantly greater accuracy in detecting small abnormalities, pre-cancerous, or cancerous cells, including micrometastates, than the related art. Thus, the pathologist does not have to base his/her analysis of a sample on his/her subjective observation of a visual image of the biological sample. Thus, for example, the pathologist may simply study the spectral image and may easily refer to the relevant portion in the registered visual image to verify his/her findings, as necessary.

In addition, the image registration method in accordance with aspects of the invention provides greater accuracy than the prior method of Bird (Bird et al., "Spectral detection of micro-metastates in lymph node histo-pathology", J. Biophoton. 2, No. 1-2, 37-46 (2009)) because it is based on correlation of digital data, i.e. the pixels in the spectral and visual images. Bird does not correlate any digital data from the images, and instead relies merely on the skill of the user to visually match spectral and visual images of adjacent tissue sections by physically overlaying the images. Thus, the image registration method in accordance with aspects of the invention provides more accurate and reproducible diagnoses with regard to abnormal or cancerous cells. This may be helpful, for example, in providing accurate diagnosis in the early stages of disease, when indicia of abnormalities and cancer are hard to detect.

In an aspect, image registration may automatically occur between a spectral image and a visual image. For example, a computing system may automatically register a spectral image and a visual image based on features of the images, as illustrated in FIGS. 5A-5C. In addition, a computing system may automatically register a spectral image and a visual image based on coordinates that are independent of image features, as illustrated in FIGS. 4A and 4B.

Figure 4A:
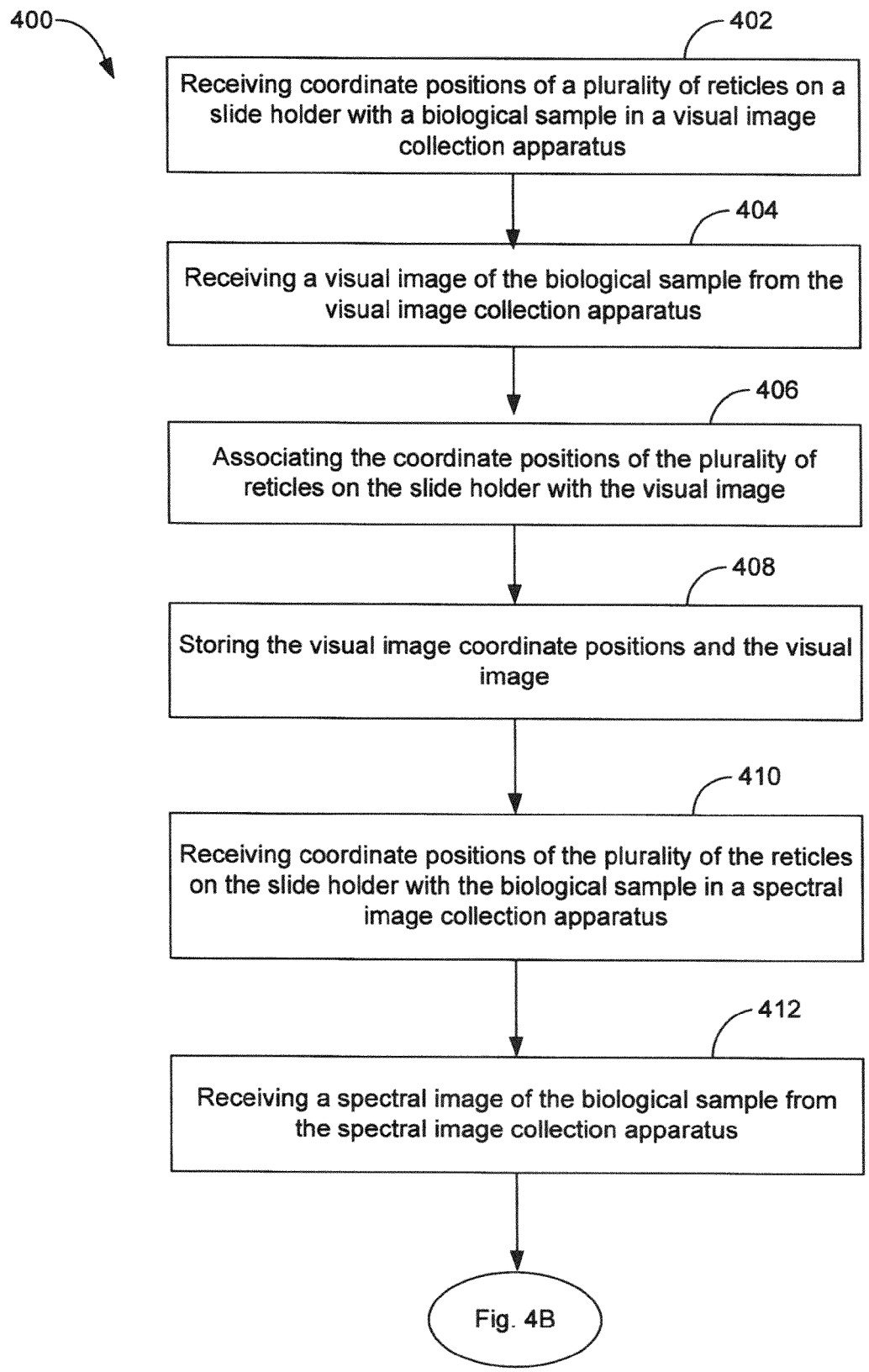
FIGS. 4A and 4B are a flowchart illustrating an example method of performing image registration on a spectral image and a visual image in accordance with aspects of the present invention.
Figure 4B:
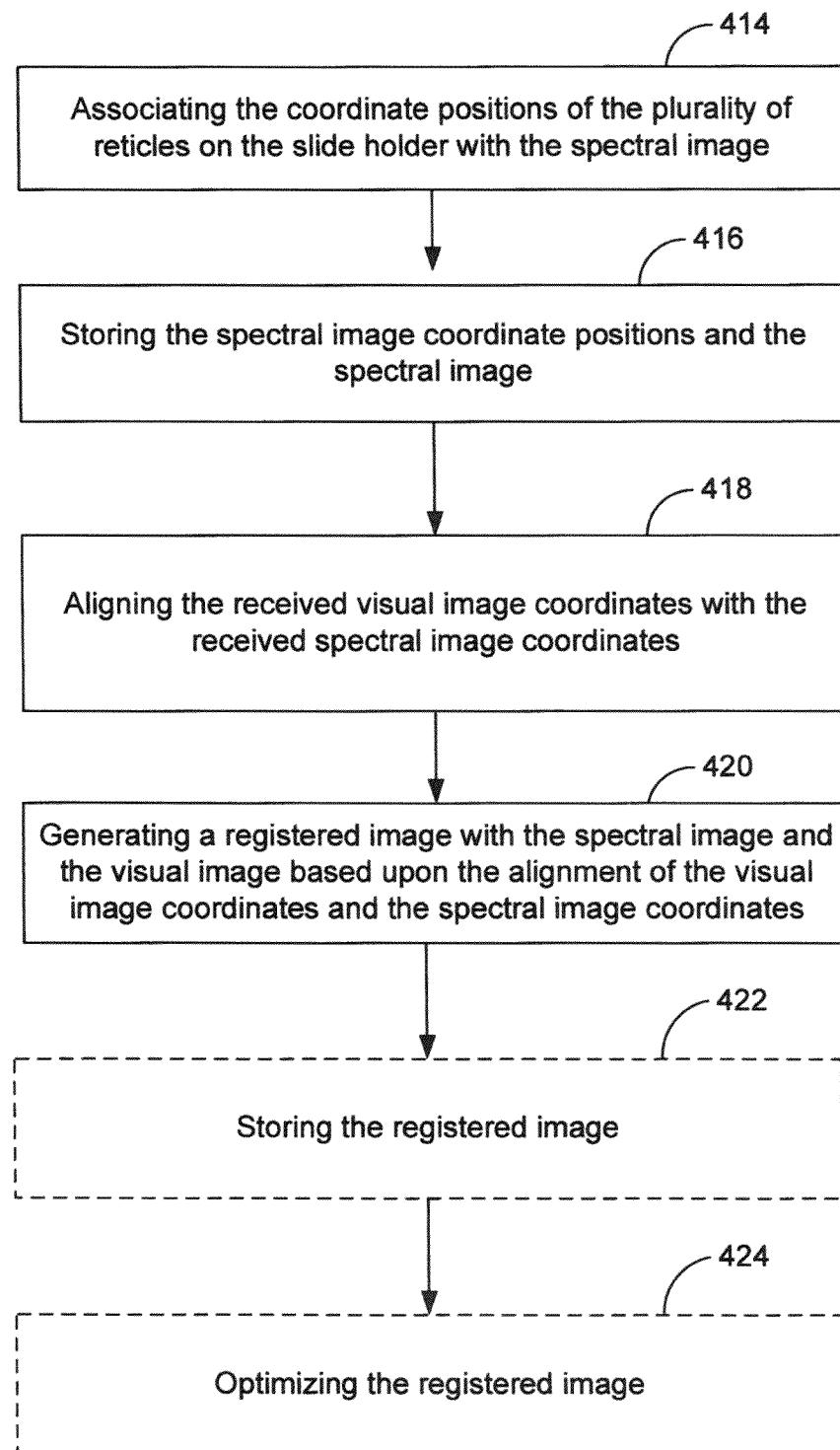
Figure 5A:
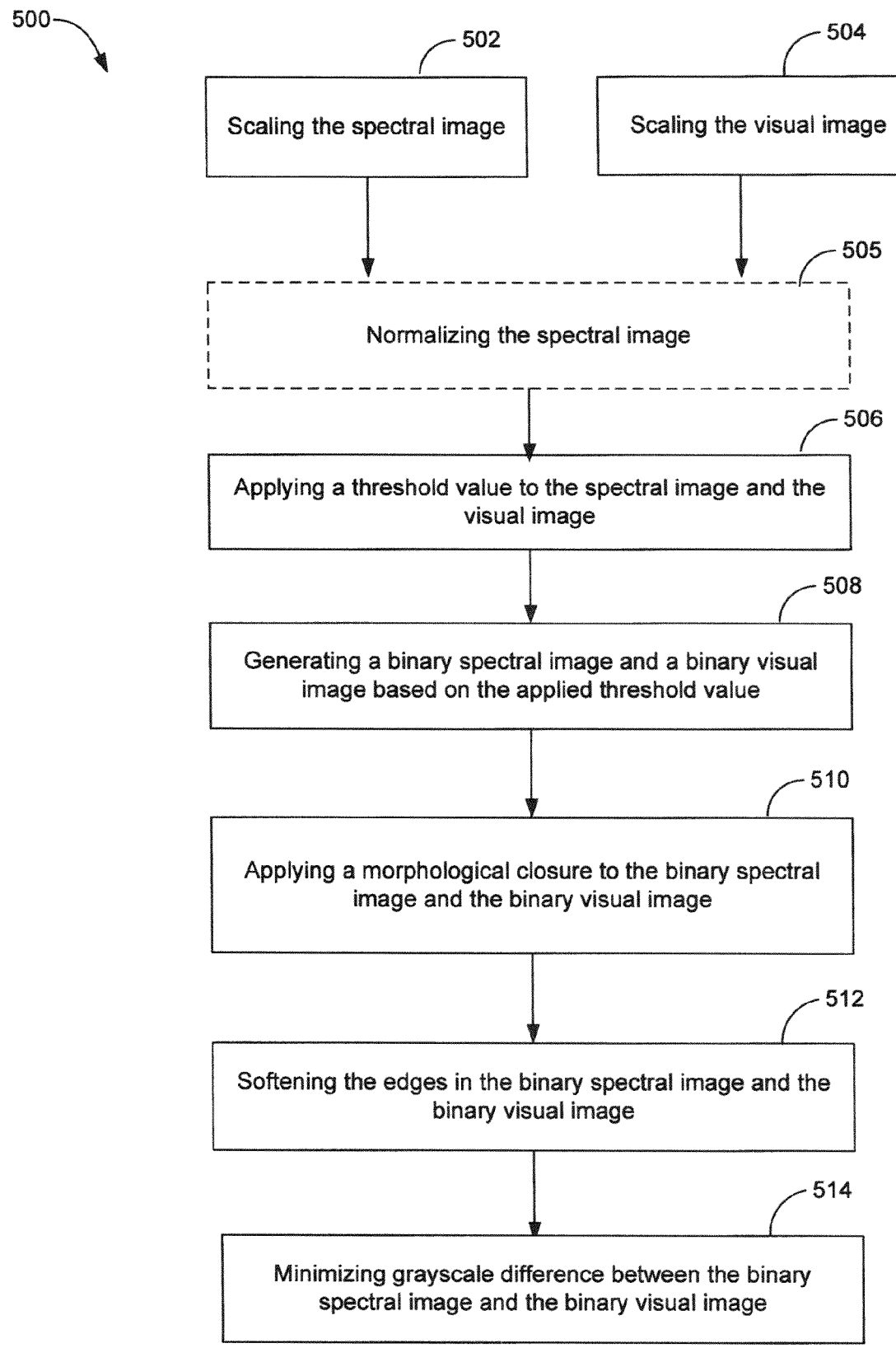
FIG. 5A is a flowchart illustrating an example method of refining image registration in accordance with aspects of the present invention.
Figure 5B:
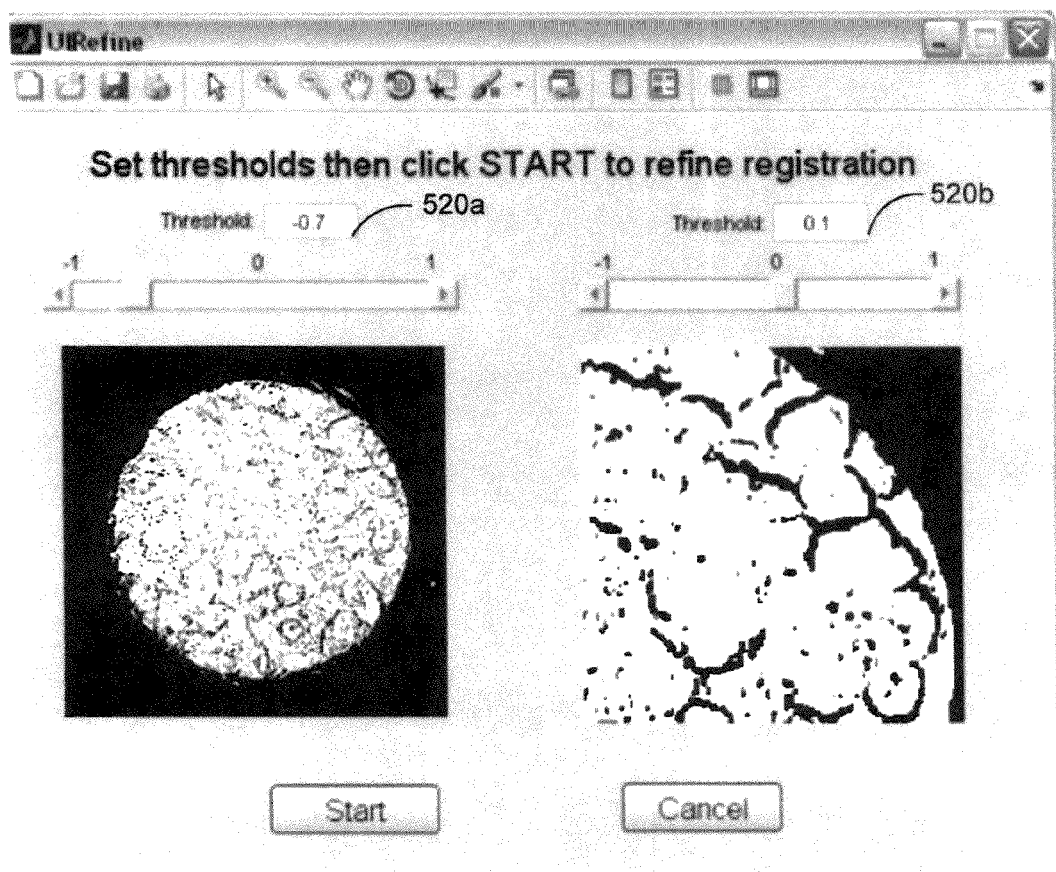
FIG. 5B is an example a graphical user interface (GUI) interface for setting a threshold value in accordance with aspects of the present invention.
Figure 5C:
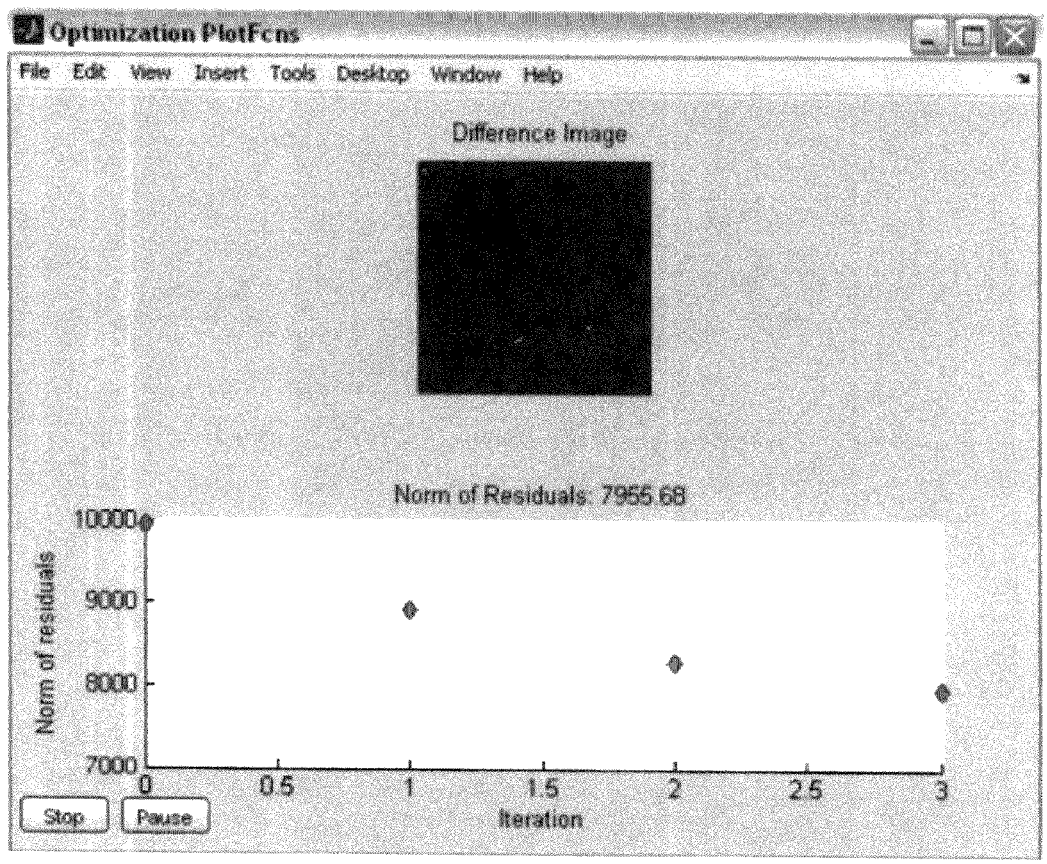
FIG. 5C is an example GUI interface illustrating an example optimization window in accordance with aspects of the present invention.

Referring now to FIGS. 4A and 4B, illustrated is an example automated method 400 for performing image registration based on coordinates that are independent of image features, in accordance with an aspect of the present invention. For example, the method may be used when the spectral image and visual image are captured using the same slide holder, such as a stage plate used with microscope stages. The slide holder may allow the biological sample to be placed with spatial accuracy and precision in each microscope.

The method may include receiving coordinate positions of a plurality of reticles on a slide holder with a biological sample in a visual collection apparatus 402. The visual collection apparatus may include, but is not limited to, a microscope that is capable of capturing an image of the biological sample. In addition, the slide holder may include a plurality of reticles marking a coordinate location on the slide holder, as illustrated in FIG. 4C.

Figure 4C:
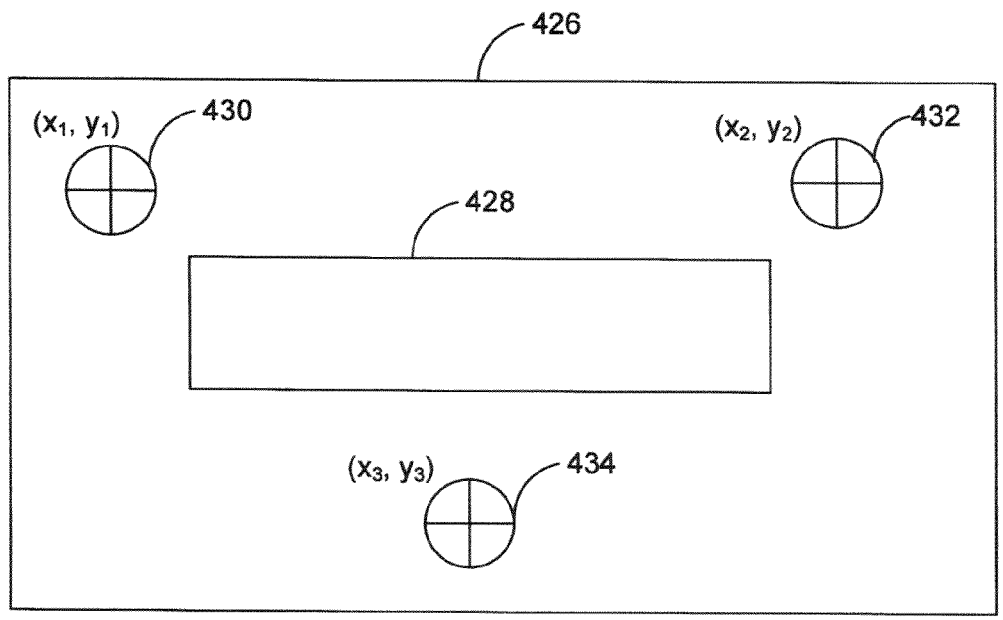
FIG. 4C illustrates an example slide holder in accordance with aspects of the present invention.

Referring now to FIG. 4C, illustrated is an example slide holder 426 in accordance with an aspect of the present invention. Slide holder 426 may include a slot 428 where the biological sample may be inserted. Biological samples may include, but are not limited to, cells and tissues. In addition, slide holder 426 may also include a plurality of reticles 430, 432, and 434 marking a position on the slide holder 426. In another aspect, the plurality of reticles may be placed directly on the slide, marking a position on the slide instead of the slide holder. Reticles 430, 432, and 434 may each have a coordinate location, e.g., an (x,y) coordinate. The coordinates from each of reticles 430, 432, and 434 may define a coordinate system that may be used during data acquisition of the biological sample. It should be noted that at least two reticles may be used to determine the coordinate system. For example, when the coordinates of two reticles are used, two solutions for the coordinate systems may be generated by the computing system. The computing system may select one of the two solutions generated based upon the orientation of the biological sample. For example, the computing system may select the solution based upon the assumption that the biological sample is not turned upside down and/or flipped. When three reticles are used to determine the coordinate system, a unique solution for the coordinate system may be generated by the computing system. Thus, as the number of reticles increase, the accuracy of the transformation may also increase and/or improve Referring back to FIG. 4A, the coordinate locations of each of the reticles on the slide holder may be received from the visual collection apparatus. In an aspect, a computing system in communication with the visual collection apparatus may receive the coordinate positions of the plurality of reticles on the slide holder. For example, the visual collection apparatus (e.g., a microscope) may be programmed to locate each of the reticles on the slide holder by moving the microscope and/or the slide holder until the reticle comes into view and transmitting the coordinate locations of the reticles to the computing system. In another aspect, a user may enter the coordinate locations of the reticles into the computing system. For example, the user may move the microscope and/or the slide holder until each reticle comes into view (and may become aligned with indicators, like crosshairs, within the microscope), and the user may enter the coordinates displayed on the microscope into the computing system. Thus, it should be noted that a variety of mechanisms, automated or otherwise, may be used to capture the coordinate position of the reticles on the slide holder and send the coordinate information to the computing system.

The method may also include receiving a visual image of the biological sample from the visual image collection apparatus 404. For example, the visual image collection apparatus may transmit the visual image of the biological sample captured by the visual image collection apparatus to the computing system.

In addition, the method may include associating the coordinate positions of the plurality of reticles on the slide holder with the visual image 406 and storing the visual image coordinate positions and the visual image 408. In an aspect, the computing system may associate the coordinate positions of the reticles received with the visual image received and store the visual image coordinate positions and the visual image, for example, in a data repository. In an aspect, the computing system may associate the file that stores the received visual image coordinates with the file that stores the received visual image.

The method may further include receiving coordinate positions of the plurality of the reticles on the slide holder with the biological sample in a spectral image collection apparatus 410. It should be noted that the same slide holder with the biological sample that is used in the visual image collection apparatus may also be used in the spectral image collection apparatus. The computing system may also be in communication with the spectral image collection apparatus and may receive the coordinate positions of each of the plurality of the reticles on the slide holder directly from the spectral image collection apparatus and/or through a user of the spectral image collection apparatus. For example, the spectral collection apparatus may be programmed to locate each of the reticles on the slide holder by moving the spectral collection apparatus and/or the slide holder until the reticle comes into view and sending the coordinate locations of the reticles to the computing system. A user may also enter the coordinate locations of the reticles into the computing system.

In addition, the method may include receiving a spectral image of the biological sample from the spectral image collection apparatus 412. The spectral image collection apparatus may transmit the captured spectral image of the biological sample to the computing system.

The method may also include associating the coordinate positions of the plurality of reticles on the slide holder with the spectral image 414 and storing the spectral image coordinates positions and the spectral image 416. The computing system may associate the received spectral image coordinates with the received spectral image. For example, the computing system may apply a label to the file storing the spectral image coordinates associating the file to the spectral image. It should also be noted that the spectral image coordinates may be stored in the same file as the spectral image.

The method may further include aligning or otherwise associating the received visual image coordinates with the received spectral image coordinates 418. The computing system may automatically map the spectral image coordinates to the visual image coordinates to create a common coordinate system between the visual image and the spectral image.

The method may additionally include generating a registered image aligning the received spectral image and the received visual image based upon the alignment of the visual image coordinates and the spectral image coordinates 420. For example, the computing system may overlay the spectral image on the visual image using the alignment of the visual image coordinates with the spectral image coordinates and automatically generate a registered image. Thus, the computing system may automatically register the spectral image with the visual image by using coordinates that are independent of the features from the spectral image and the visual image.

The method may optionally include storing the registered image 422. The computing system may store the registered image in a data repository so that a user of the computing system may access the registered image and/or make changes to the registered image.

In addition, the method may optionally include optimizing the registered image 424. For example, the computing system may apply one or more optimizations to find the best rigid body transforms that will cause the visual image coordinate points and the spectral image coordinate points to align or correspond. The computing system may use one or more optimizations to improve the accuracy of a registered image by attempting to further align the images.

One optimization may include minimizing the distance between the spectral image and the visual images in the overlaid images that are mapped in the same coordinate system. The distance may be a measure of the grayscale pixel-by-pixel errors summed over the whole image. For example, the optimization may include:

$$\min(p) J = \text{sum } D(p, I1, I2)$$

$$D = I2(p) - I1$$

where p is the same scaled rigid body transformation used for the select points or reticle-based registration, D(p, •, •) is the distance measure (which is applied pixel-by-pixel), and I2(p) is the I2 image transformed by p into the same space as I1. I1 and I2 images may be created by applying a series of transformations to the spectral and visual images in order to get the images into the same grayscale space because the visual pixel values may not directly compared to the HCA or spectral pixel values.

Another optimization may include minimizing the least squared error between the pairs of points selected in the two images (e.g., the visual image and the spectral image). In an aspect, the computing system may perform an optimization to minimize the least squared error between the pairs of points selected in the two images (e.g., the visual image and the spectral image). For example, the optimization may include:

$$\min_p J = \sum_{i,j} (x_i - x_j)^2 + (y_i - y_j)^2$$

where $(x_i, y_i)$ are selected reference points in the visual image, $(x_j, y_j)$ are the reference points from the spectral image after they are mapped to the visual image, and $p=[u\ v\ \lambda\ \theta]$ are the registration parameters.

It should be noted that various optimization settings may be used by the computing system to provide optimization limits on the optimizations being performed by the computing system. For example, optimization limits may include, but are not limited to, a maximum number of function evaluations, convergence tolerances, and/or an upper and a lower bound on the transformation parameters. The upper and lower bounds may be advantageous in preventing the optimization from venturing too far outside of a desired solution.

Referring now to FIG. 5A, illustrated is an example method 500 for refining image registration based on image features in accordance with an aspect of the present invention. The computing system may refine an image registration when the overlay of the visual image with the spectral image does not correspond well. For example, the overlay of the images may display the features of the biological sample out of alignment between the visual image and the spectral image. In an aspect, the computing system may automatically perform the method for refining the image registration to align the image features from the spectral image with the visual image as precisely as possible. It should be noted that the computing system may also switch between a first spectral image level and a different spectral image level, for example, if the first spectral image level does not contain sufficient useful information in the spectral image when the registration occurs.

The method may include scaling the spectral image 502 and scaling the visual image 504. Scaling may be performed so that the morphological (e.g., shape) features of interest are approximately the same size in each image. Scaling may be based upon the ratios between the spectral image and the visual images. For example, the visual image may have a higher resolution than the spectral image, and therefore, the scaling may include setting an upper and lower bound on the images to scale the higher resolution image to a lower resolution image. Example scaling equations that the computing system may use include the following:

$$x_{H\&E} = u + \lambda^*(x_{HCA}^* \cos\theta - y_{HCA}^* \sin\theta)$$

$$y_{H\&E} = v + \lambda^*(y_{HCA}^* \sin\theta + y_{HCA}^* \cos\theta)$$

where (u,v) represents a translation, $\lambda$ a scale factor and $\theta$ a rotation. The scaling may be applied to selected spectral image reference points (e.g., reticle coordinates and/or registration points selected by a user) and to map the selected spectral image reference points to the visual image reference points (e.g., reticle coordinates and/or registration points selected by the user).

In an aspect, the computing system may perform an optimization to minimize a registration distance function between all the points in the registered images. For example, the optimization may include:

$$\min_p J = \sum_{i,j} (I(p)_{i,j} - T_{i,j})^2$$

where image $T_{ij}$ is based on the visual image, $I(p)_{ij}$ is based on the spectral image further transformed by the scaled rigid body transform $p=[u\ v\ \lambda\ \theta]$ and interpolated into the same coordinate frame as T. The sum is over all pixels (i,j) in the images. While this optimization uses the grayscale distance function $D=I(p)-T$, it should be noted that other distance functions may be used in the optimization, such as the normalized gradient field. The images T and I are interpolated, filtered and converted versions of the visual and spectral images as required by the particular distance function being used. Different distance functions may require different conversions and filtering of the visual and spectral images.

The method may optionally include normalizing the spectral image 505. In an aspect, the computing system may normalize the spectral image to improve the image features of the spectral images. For example, when the normalized spectral image is compared with the visual image, the features in the normalized spectral image may appear sharper and provide a more accurate representation of the image features.

In an aspect, the computing system may apply a weighted normalization to the spectral image. Using a weighted normalization on the spectral image may be beneficial, for example, because the infrared absorption spectrum of a cell or tissue pixel is dominated by the protein vibrations. Since proteins contribute over 60% of a cell's dry mass, whereas nucleic acids (DNA and RNA) contribute about 20% or less of a cell's dry mass. Therefore, the vibrations of proteins (observed predominantly in the amide I and II regions, between 1700 and 1500 cm$^{-1}$) may be much more prominent in the spectra than the features of nucleic acids, which may be observed mostly in the symmetric (ca. 1090 cm$^{-1}$) and antisymmetric (ca. 1230 cm$^{-1}$) phosphodiester stretching vibrations. Since changes in nucleic acid vibrational bands are frequently observed with the onset of cancerous disease, it may be advantageous to utilize normalization procedures that emphasize the low wavenumber spectral region of spectra in a data set. This approach may be advantageous, for example, when carrying out hierarchical cluster analysis (HCA) for the initial partition of the spectral data set.

In an aspect, the weighted normalization may include a ramp function with a value of 1 at the low wavenumber limit of the spectrum (typically 778 cm$^{-1}$) and a value of 0 at the high wavenumber limit (typically 1800 cm$^{-1}$) multiplied by the spectral vector after standard vector normalization (e.g., "the ramp method"). The product of this function may include a weighted spectral vector in which the importance of the protein region is suppressed.

In another aspect, the weighted normalization may include region normalization. In region normalization, the spectrum S is divided into two or more (for example 2 or 3) regions, such that the protein and nucleic acid spectral features fall within different regions (for example: region 1 from 1800 to 1480 $cm^{-1}$, and region 2 from 1478 to 778 $cm^{-1}$). The two (or more) regions may be vector normalized separately, adding more weight to the low intensity spectral regions. Although "region normalization" may cause a discontinuity (for example, between 1478 and 1480 $cm^{-1}$) in the spectra, this method may result in better discrimination of normal and cancerous regions, for example, as measured by the number of clusters required in HCA for the discrimination of normal and cancerous regions.

The computing system may also perform the weighted normalization on the spectral image to improve the features of the spectral image to aid in the refinement of the registered image.

The method may also include applying a threshold value to the spectral image and the visual image 506 and generating a binary spectral image and a binary visual image based on the applied threshold value 508. The computing system may automatically select a threshold value to apply to the spectral image and a threshold value to apply to the visual image. In addition, the computing system may receive the threshold values from a user of the computing system.

Referring now to FIG. 5B, illustrated is an example GUI interface that allows a user to select a threshold value for the visual image 520a and the spectral image 520b. For example, the user may use sliders to set the threshold values. As the user moves the sliders, the tissues in both images may change color (e.g., black to white or white to black) and the shapes in or other aspects of the images may become more or less visible or distinct, for example. The user may select a threshold value for each of the spectral image and the visual image when the tissues in both images become the same color/shade (e.g., black or white) and common shapes in each image may become visible without a lot of noise in the image. It should be noted that the threshold values for the spectral image and the visual image may be the same number and/or may be a different number.

Referring back to FIG. 5A, the computing system may receive the selected threshold values and generate a binary spectral image and a binary visual image based on the applied threshold values. For example, each pixel with a number above the threshold value may be converted to white, while each pixel with a number below the threshold value may be converted to black. The computing system may map all the pixels in the spectral image and the visual image into black and white using the threshold values for each respective image. By generating a binary image (e.g., a black and white image), the interstitial spaces between the tissues may be highlighted, as well as the basic structure of the biological sample, any morphological (e.g., shape) features in the biological sample, and/or the shape of stained regions within the tissue (e.g., as a result of staining the biological sample, for example, with an IHC agent). Thus, any shape that may occur in the visual image that also occurs in the spectral image could be highlighted.

In addition, the computing system may display a difference image illustrating the difference between the spectral binary image and one or both of the visual binary image and the registered image. Referring now to FIG. 5C, illustrated is an example GUI screen with a difference image illustrated and a graph with points illustrating the progress in minimizing the error in the difference image. The difference image provides a visual indication of the accuracy of the fit of the registered images. In an aspect, the difference image may be as black in color as possible. If the difference image includes frequent white spaces, this result may indicate the presence of error in the registered image (e.g., the overlay of the images illustrates image features out of alignment). As illustrated in the graph, multiple iterations of the threshold selection may occur before the difference image illustrates minimum error (e.g., a mostly black image) in the threshold selections. It should be noted that the iteration process may terminate if a maximum number of iterations is reached before the error is minimized in the difference image.

Referring back to FIG. 5A, the computing system may continue to apply various threshold values until a minimum error value is reached for the binary spectral image and the visual spectral image and/or until a maximum number of iterations are reached, whichever occurs first.

The method may also include applying a morphological closure to the binary spectral image and the binary visual image 510. The morphological closure may remove noise from the binary images by smoothing any tiny dots that may appear in the binary images into white areas. For example, the computing system may apply the morphological closure to the binary images by adding a boundary to the images and converting the dots to white into white areas and/or removing small black or white dots within larger white or black areas, respectively.

In addition, the method may include softening the edges in the binary spectral image and the binary visual image 512. In an aspect, the computing system may apply a Gaussian filter to blur the ramps between the black and white edges in the binary images. For example, the computing system may smooth across the edges to blur the edges and make them softer, in order to improve convergence of the optimization.

The method may further include minimizing the grayscale difference between the binary spectral image and the binary visual image 514. For example, the computing system may apply one or more of the optimizations discussed above in 502-512 to minimize the grayscale difference between the spectral image and the binary image in order to obtain registration parameters with a better fit. It should be noted that the optimization process may repeat until the structures in the spectral image and the visual image are aligned as close as possible in the registered image.

Training

A training set may optionally be developed, as set forth in step 305 in the method provided in the flowchart of FIG. 3. According to aspects of the invention, a training set includes spectral data that is associated with specific diseases or conditions, among other things. The association of diseases or conditions to spectral data in the training set may be based on a correlation of classical pathology to spectral patterns based on morphological features normally found in pathological specimens. The diseases and conditions may include, but are not limited to, cellular abnormalities, inflammation, infections, pre-cancer, and cancer.

According to one aspect in accordance with the invention, in the training step, a training set may be developed by identifying a region of a visual image containing a disease or condition, correlating the region of the visual image to spectral data corresponding to the region, and storing the association between spectral data and the corresponding disease or condition. The training set may then be archived in a repository, such as a database, and made available for use in machine learning algorithms to provide a diagnostic algorithm with output derived from the training set. The diagnostic algorithm may also be archived in a repository, such as a database, for future use.

For example, a visual image of a tissue section may be registered with a corresponding unsupervised spectral image, such as one prepared by HCA. Then, a user may select a characteristic region of the visual image. This region may be classified and/or annotated by a user to specify a disease or condition. The spectral data underlying the characteristic region in the corresponding registered unsupervised spectral image may be classified and/or annotated with the disease or condition.

The spectral data that has been classified and/or annotated with a disease or condition provides a training set that may be used to train a supervised analysis method, such as an ANN. Such methods are also described, for example, in Lasch, Miljkovic Dupuy. The trained supervised analysis method may provide a diagnostic algorithm.

A disease or condition information may be based on algorithms that are supplied with the instrument, algorithms trained by a user, or a combination of both. For example, an algorithm that is supplied with the instrument may be enhanced by the user.

An advantage of the training step according to aspects of the invention is that the registered images may be trained against the best available, consensus-based "gold standards", which evaluate spectral data by reproducible and repeatable criteria. Thus, after appropriate instrument validation and algorithm training, methods in accordance with aspects of the invention may produce similar results worldwide, rather than relying on visually-assigned criteria such as normal, atypical, low grade neoplasia, high grade neoplasia, and cancer. The results for each cell may be represented by an appropriately scaled numeric index or the results overall as a probability of a classification match. Thus, methods in accordance with aspects of the invention may have the necessary sensitivity and specificity for the detection of various biological structures, and diagnosis of disease.

The diagnostic limitation of a training set may be limited by the extent to which the spectral data are classified and/or annotated with diseases or conditions. As indicated above, this training set may be augmented by the user's own interest and expertise. For example, a user may prefer one stain over another, such as one or many IHC stains over an H&E stain. In addition, an algorithm may be trained to recognize a specific condition, such as breast cancer metastases in axillary lymph nodes, for example. The algorithm may be trained to indicate normal vs. abnormal tissue types or binary outputs, such as adenocarcenoma vs. not-adenocarcenoma only, and not to classify the different normal tissue types encountered, such as capsule, B- and T-lymphocytes. The regions of a particular tissue type, or states of disease, obtained by SHP, may be rendered as "digital stains" superimposed on real-time microscopic displays of the tissue sections.

Diagnosis, Prognosis, Predictive, Thernostic

Once the spectral and visual images have been registered, they may be used make a medical diagnosis, as outlined in step 306 in the flowchart of FIG. 3. The diagnosis may include a disease or condition including, but not limited to, cellular abnormalities, inflammation, infections, pre-cancer, cancer, and gross anatomical features. In a method according to aspects of the invention, spectral data from a spectral image of a biological specimen of unknown disease or condition that has been registered with its visual image may be input to a trained diagnostic algorithm, as described above. Based on similarities to the training set that was used to prepare the diagnostic algorithm, the spectral data of the biological specimen may be correlated to a disease or condition. The disease or condition may be output as a diagnosis.

For example, spectral data and a visual image may be acquired from a biological specimen of unknown disease or condition. The spectral data may be analyzed by an unsupervised method, such as HCA, which may then be used along with spatial reference data to prepare an unsupervised spectral image. This unsupervised spectral image may be registered with the visual image, as discussed above. The spectral data that has been analyzed by an unsupervised method may then be input to a trained supervised algorithm. For example, the trained supervised algorithm may be an ANN, as described in the training step above. The output from the trained supervised algorithm may be spectral data that contains one or more labels that correspond to classifications and/or annotations of a disease or condition based on the training set.

To extract a diagnosis based on the labels, the labeled spectral data may used to prepare a supervised spectral image that may be registered with the visual image and/or the unsupervised spectral image of the biological specimen. For example, when the supervised spectral image is registered with the visual image and/or the unsupervised spectral image, through a GUI, a user may select a point of interest in the visual image or the unsupervised spectral image and be provided with a disease or condition corresponding to the label at that point in the supervised spectral image. As an alternative, a user may request a software program to search the registered image for a particular disease or condition, and the software may highlight the sections in any of the visual, unsupervised spectral, and supervised spectral images that are labeled with the particular disease or condition. This advantageously allows a user to obtain a diagnosis in real-time, and also allows the user view a visual image, which he/she is familiar with, while accessing highly sensitive spectroscopically obtained data.

The diagnosis may include a binary output, such as an "is/is not" type output, that indicates the presence or lack of a disease or condition. In addition, the diagnosis may include, but is not limited to an adjunctive report, such as a probability of a match to a disease or condition, an index, or a relative composition ratio.

In accordance with aspects of the method of the invention, gross architectural features of a tissue section may be analyzed via spectral patterns to distinguish gross anatomical features that are not necessarily related to disease. Such procedures, known as global digital staining (GDS), may use a combination of supervised and unsupervised multivariate methods. GDS may be used to analyze anatomical features including, but not limited to, glandular and squamous epithelium, endothelium, connective tissue, bone, and fatty tissue.

In GDS, a supervised diagnostic algorithm may be constructed from a training dataset that includes multiple samples of a given disease from different patients. Each individual tissue section from a patient may be analyzed as described above, using spectral image data acquisition, pre-processing of the resulting dataset, and analysis by an unsupervised algorithm, such as HCA. The HCA images may be registered with corresponding stained tissue, and may be annotated by a pathologist. This annotation step, indicated in FIGS. 15A-C, allows the extraction of spectra corresponding to typical manifestation of tissue types or disease stages and states, or other desired features. The resulting typical spectra, along with their annotated medical diagnosis, may subsequently be used to train a supervised algorithm, such as an ANN, that is specifically suited to detect the features it was trained to recognize.

According to the GDS method, the sample may be stained using classical stains or immuno-histochemical agents. When the pathologist receives the stained sample and inspects it using a computerized imaging microscope, the spectral results may be available to the computer controlling the visual microscope. The pathologist may select any tissue spot on the sample and receive a spectroscopy-based diagnosis. This diagnosis may overlay a grayscale or pseudo-color image onto the visual image that outlines all regions that have the same spectral diagnostic classification.

Figure 15A:
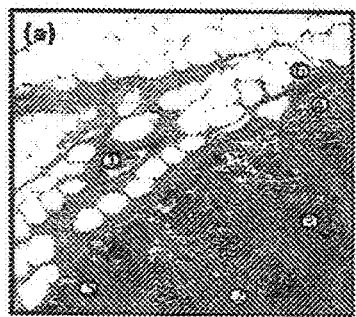
FIG. 15A is a visual microscopic image of H&E-stained lymph node tissue section according to aspects of the invention.
Figure 15B:
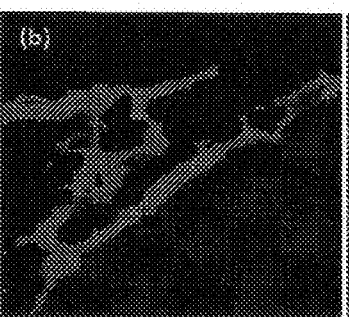
FIG. 15B is a global digital staining image of section shown in FIG. 15A, distinguishing capsule and interior of lymph node according to aspects of the invention.

FIG. 15A is a visual microscopic image of H&E-stained lymph node tissue section. FIG. 15B shows a typical example of global discrimination of gross anatomical features, such as capsule and interior of lymph node. FIG. 15B is a global digital staining image of section shown in FIG. 15A, distinguishing capsule and interior of lymph node.

Figure 15C:
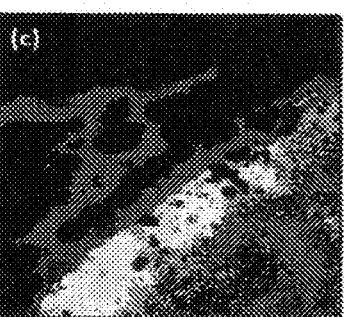
FIG. 15C is a diagnostic digital staining image of the section shown in FIG. 15A, distinguishing capsule, metastatic breast cancer, histiocytes, activated B-lymphocytes, and T-lymphocytes according to aspects of the invention.

Areas of these gross anatomical features, which are registered with the corresponding visual image, may be selected for analysis based on more sophisticated criteria in the spectral pattern dataset. This next level of diagnosis may be based on a diagnostic marker digital staining (DMDS) database, which may be solely based on SHP results, for example, or may contain spectral information collected using immuno-histochemical (IHC) results. For example, a section of epithelial tissue may be selected to analyze for the presence of spectral patterns indicative of abnormality and/or cancer, using a more diagnostic database to scan the selected area. An example of this approach is shown schematically in FIG. 15C, which utilizes the full discriminatory power of SHP and yields details of tissue features in the lymph node interior (such as cancer, lymphocytes, etc.), as may be available only after immune-histochemical staining in classical histopathology. FIG. 15C is a DMDS image of section shown in FIG. 15A, distinguishing capsule, metastatic breast cancer, histiocytes, activated B-lymphocytes and T-lymphocytes.

Figure 16:
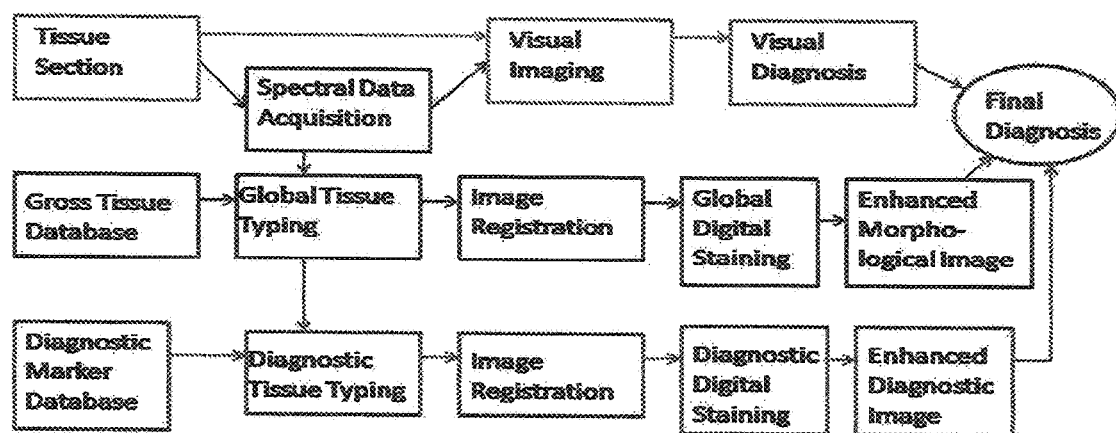
FIG. 16 is a schematic of relationship between global and diagnostic digital staining according to aspects of the invention.

The relationship between GDS and DMDS is shown by the horizontal progression marked in dark blue and purple, respectively, in the schematic of FIG. 16. Both GDS and DMDS are based on spectral data, but may include other information, such as IHC data. The actual diagnosis may also be carried out by the same or a similarly trained diagnostic algorithm, such as a hANN. Such a hANN may first analyze a tissue section for gross anatomical features detecting large variance in the dataset of patterns collected for the tissue (the dark blue track). Subsequent "diagnostic element" analysis may be carried out by the hANN using a subset of spectral information, shown in the purple track. A multi-layer algorithm in binary form may be implemented, for example. Both GDS and DMDS may use different database subsections, shown as Gross Tissue Database and Diagnostic Tissue Database in FIG. 16, to arrive at the respective diagnoses, and their results may be superimposed on the stained image after suitable image registration.

According to an example method in accordance with aspects of the invention, a pathologist may provide certain inputs to ensure that an accurate diagnosis is achieved. For example, the pathologist may visually check the quality of the stained image. In addition, the pathologist may perform selective interrogation to change the magnification or field of view of the sample.

The method according to aspects of the invention may be performed by a pathologist viewing the biological specimen and performing the image registration. Alternatively, since the registered image contains digital data that may be transmitted electronically, the method may be performed remotely.

Methods may be demonstrated by the following non-limiting examples.

Example 2

Lymph Node Section

FIG. 17 shows a visual image of an H&E-stained axillary lymph node section measuring 1 mm×1 mm, containing a breast cancer micrometastasis in the upper left quadrant. FIG. 17B is a SHP-based digitally stained region of breast cancer micrometastasis. By selecting, for example, by clicking using a cursor controlled mouse, in the general area of the micrometastasis, a region that was identified by SHP to be cancerous is highlighted in red as shown in FIG. 17B. FIG. 17C is a SHP-based digitally stained region occupied by B-lymphocyes. By pointing toward the lower right corner, regions occupied by B-lymphocyte are marked in light blue, as shown in FIG. 17C. FIG. 17D is a SHP-based digitally stained region that shows regions occupied by histocytes, which are identified by the arrow.

Figure 17A:
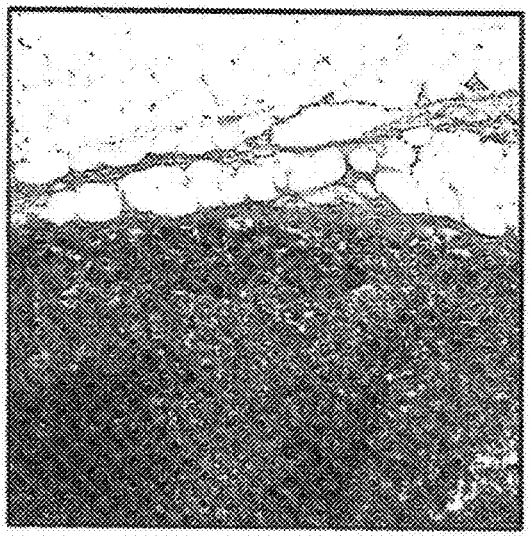
FIG. 17A is a visual image of H&E-stained tissue section from an axillary lymph node according to aspects of the invention.
Figure 17B:
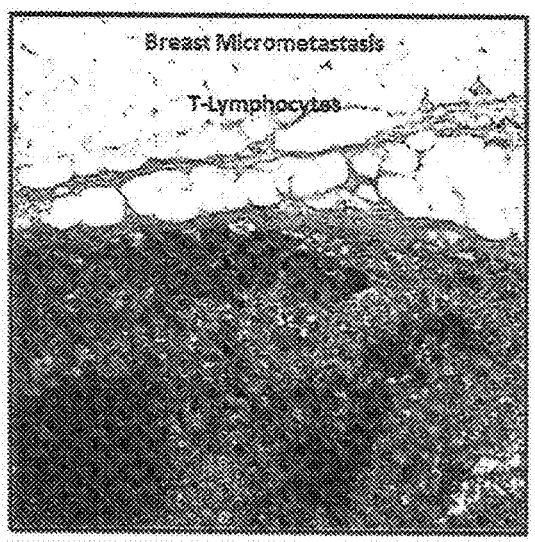
FIG. 17B is a SHP-based digitally stained region of breast cancer micrometastasis according to aspects of the invention.
Figure 17C:
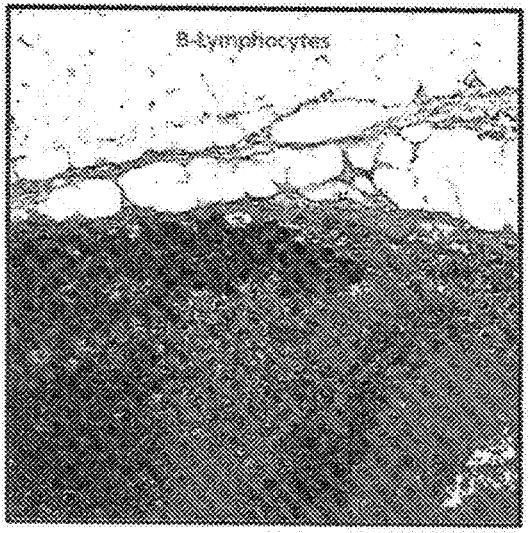
FIG. 17C is a SHP-based digitally stained region occupied by B-lymphocyes according to aspects of the invention.
Figure 17D:
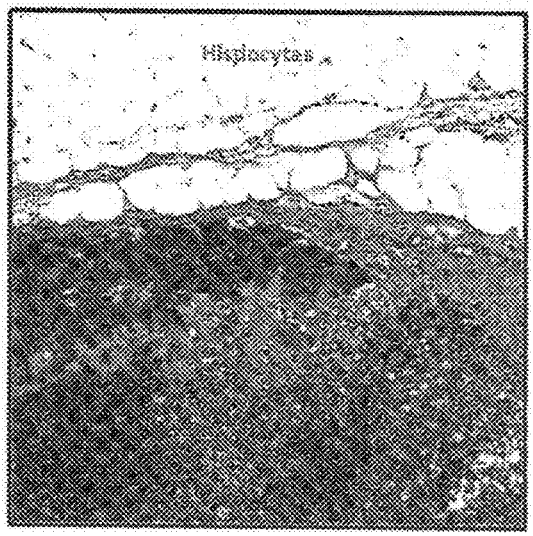
FIG. 17D is a SHP-based digitally stained region occupied by histocytes according to aspects of the invention.
Figure 18:
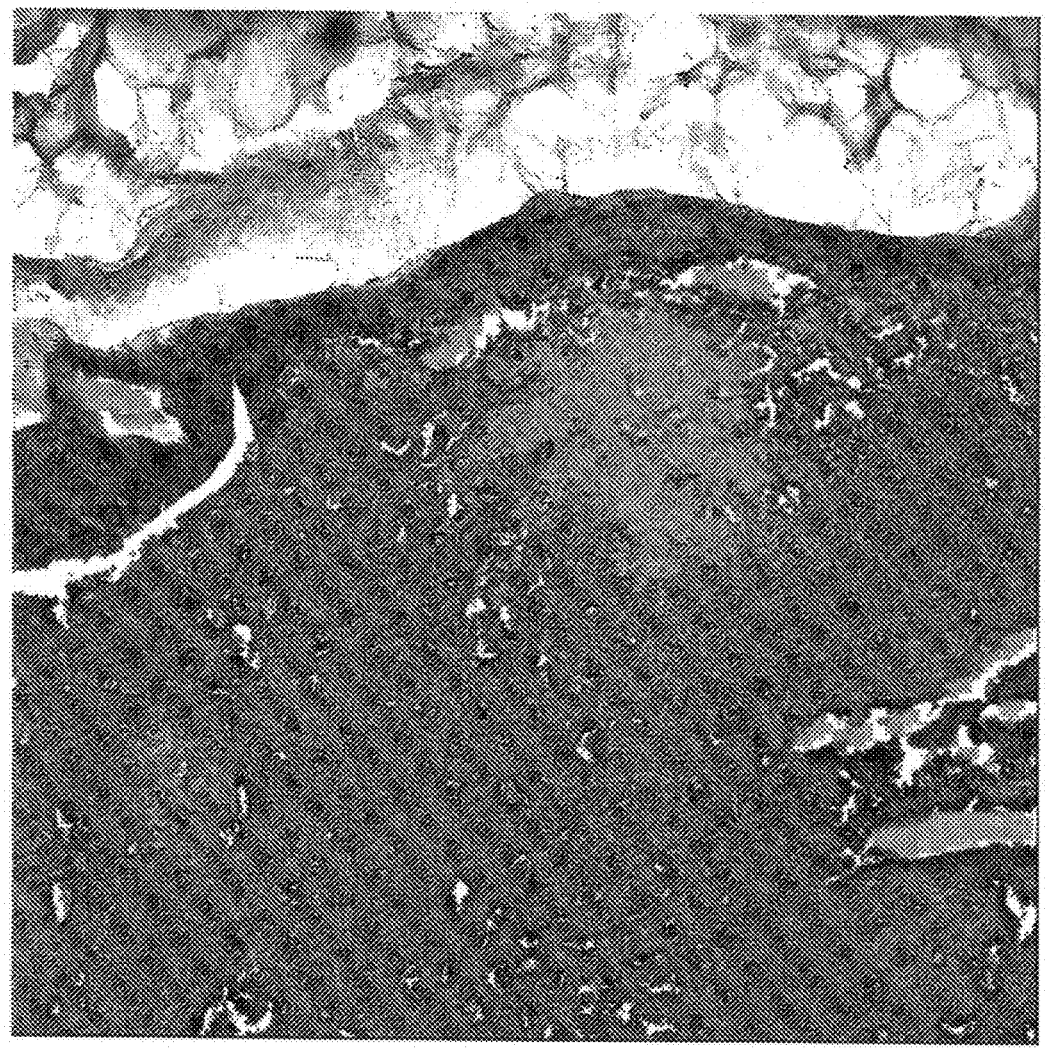
FIG. 18 illustrates the detection of individual cancer cells, and small clusters of cancer cells via SHP according to aspects of the invention.

Since the SHP-based digital stain is based on a trained and validated repository or database containing spectra and diagnoses, the digital stain rendered is directly relatable to a diagnostic category, such as "metastatic breast cancer," in the case of FIG. 17B. The system may be first used as a complementary or auxiliary tool by a pathologist, although the diagnostic analysis may be carried out by SHP. As an adjunctive tool, the output may be a match probability and not a binary report, for example. FIG. 18 shows the detection of individual and small clusters of cancer cells with SHP.

Example 3

Fine Needle Aspirate Sample of Lung Section

Sample sections were cut from formalin fixed paraffin embedded cell blocks that were prepared from fine needles aspirates of suspicious legions located in the lung. Cell blocks were selected based on the criteria that previous histological analysis had identified an adenocarcinoma, small cell carcinoma (SCC) or squamous cell carcinoma of the lung. Specimens were cut by use of a microtome to provide a thickness of about 5 µm and subsequently mounted onto low-e microscope slides (Kevley Technologies, Ohio, USA). Sections were then deparaffinized using standard protocols. Subsequent to spectroscopic data collection, the tissue sections were hematoxylin and eosin (H&E) stained to enable morphological interpretations by a histopathologist.

A Perkin Elmer Spectrum 1/Spotlight 400 Imaging Spectrometer (Perkin Elmer Corp, Shelton, Conn., USA) was employed in this study. Infrared micro-spectral images were recorded from 1 mm×1 mm tissue areas in transflection (transmission/reflection) mode, with a pixel resolution of 6.25 µm×6.25 µm, a spectral resolution of 4 $cm^{-1}$, and the co-addition of 8 interferograms, before Norton-Beer apodization (see, e.g., Naylor, et al. J Opt. Soc. Am., A24:3644-3648 (2007)) and Fourier transformation. An appropriate background spectrum was collected outside the sample area to ratio against the single beam spectra. The resulting ratioed spectra were then converted to absorbance. Each 1 mm×1 mm infrared image contains 160×160, or 25,600 spectra.

Initially, raw infrared micro-spectral data sets were imported into and processed using software written in Matlab (version R2009a, Mathworks, Natick, Mass., USA). A spectral quality test was performed to remove all spectra that were recorded from areas where no tissue existed, or displayed poor signal to noise. All spectra that pass the test were then baseline off-set normalized (subtraction of the minimal absorbance intensity across the entire spectral vector), converted to second derivative (Savitzy-Golay algorithm (see, e.g., Savitzky, et al. Anal. Chem., 36:1627 (1964)), 13 smoothing points), cut to only include intensity values recorded in the $1350\ cm^{-1}$-$900\ cm^{-1}$ spectral region, and finally vector normalized.

Processed data sets were imported into a software system and HCA performed using the Euclidean distance to define spectral similarity, and Ward's algorithm (see, e.g., Ward, J Am. Stat. Assoc., 58:236 (1963)) for clustering. Pseudo-color cluster images that describe pixel cluster membership, were then assembled and compared directly with H&E images captured from the same sample. HCA images of between 2 and 15 clusters, which describe different clustering structures, were assembled by cutting the calculated HCA dendrogram at different levels. These cluster images were then provided to collaborating pathologists who confirmed the clustering structure that best replicated the morphological interpretations they made upon the H&E-stained tissue.

Infrared spectra contaminated by underlying base line shifts, unaccounted signal intensity variations, peak position shifts, or general features not arising from or obeying LambertBeer law were corrected by a sub-space model version of EMSC for Mie scattering and reflection contributions to the recorded spectra (see B. Bird, M. Miljković and M. Diem, "Two step resonant Mie scattering correction of infrared micro-spectral data: human lymph node tissue", J. Biophotonics, 3 (8-9) 597-608 (2010)). Initially, 1000 recorded spectra for each cancer type were pooled into separate data sets from the infrared images presented in FIG. 19A-19F.

Figure 19A:
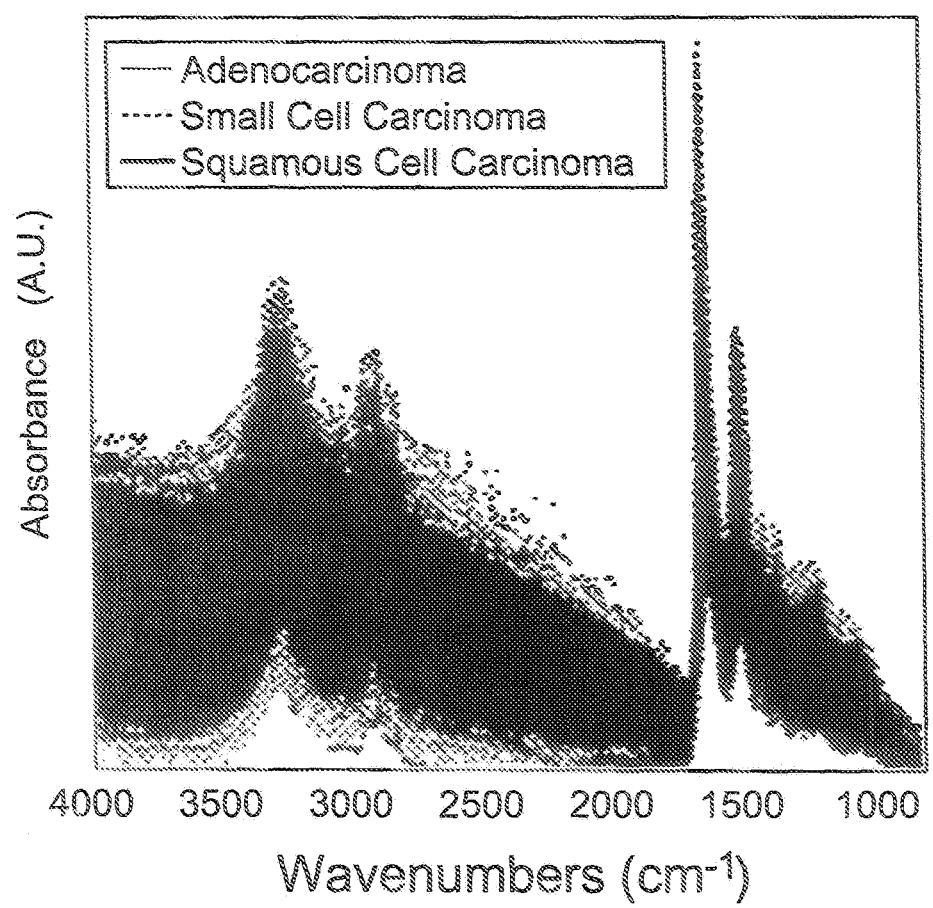
FIG. 19A shows raw spectral data sets comprising cellular spectra recorded from lung adenocarcinoma, small cell carcinoma, and squamous cell carcinoma cells according to aspects of the invention.
Figure 19B:
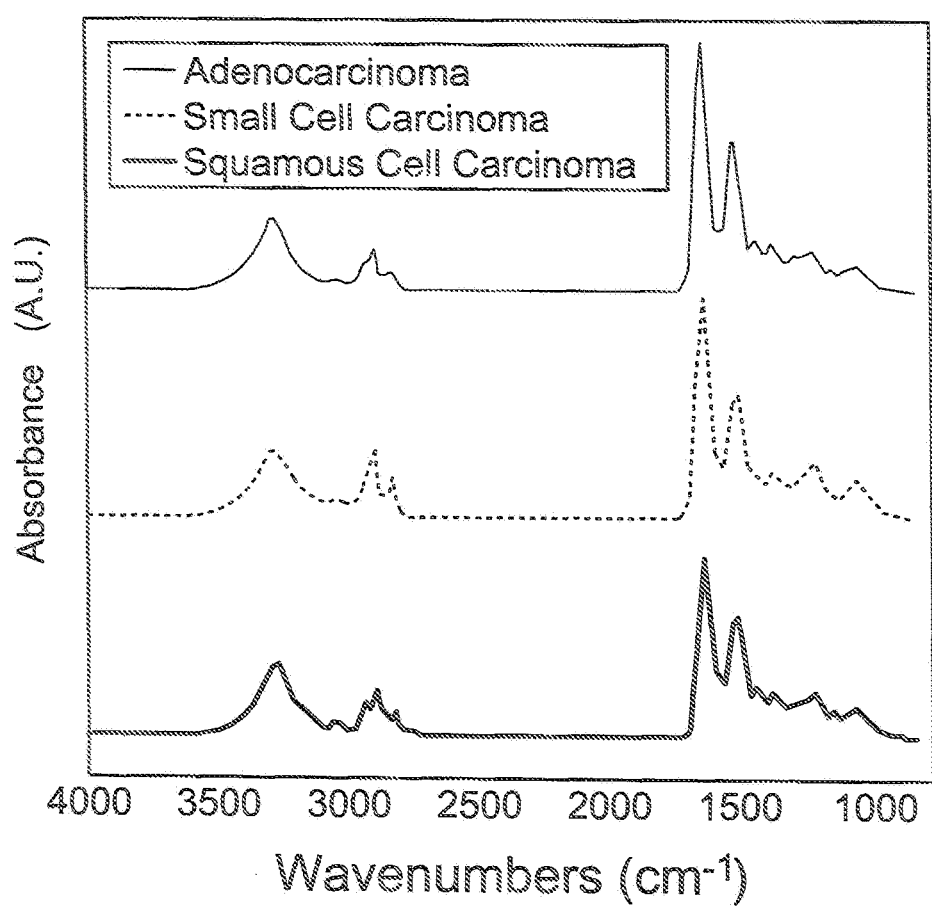
FIG. 19B shows corrected spectral data sets comprising cellular spectra recorded from lung adenocarcinoma, small cell carcinoma, and squamous cell carcinoma cells according to aspects of the invention.

These data sets were then searched for spectra with minimal scattering contributions, a mean for each cancer type was calculated to increase signal to noise, and KK transforms were calculated for each cell type, as shown in FIG. 19A and FIG. 19B. FIG. 19A shows raw spectral data sets comprising cellular spectra recorded from lung adenocarcinoma, small cell carcinoma, and squamous cell carcinoma cells. FIG. 19B shows corrected spectral data sets comprising cellular spectra recorded from lung adenocarcinoma, small cell carcinoma, and squamous cell carcinoma cells, respectively. FIG. 19C shows standard spectra for lung adenocarcinoma, small cell carcinoma, and squamous cell carcinoma.

Figure 19D:
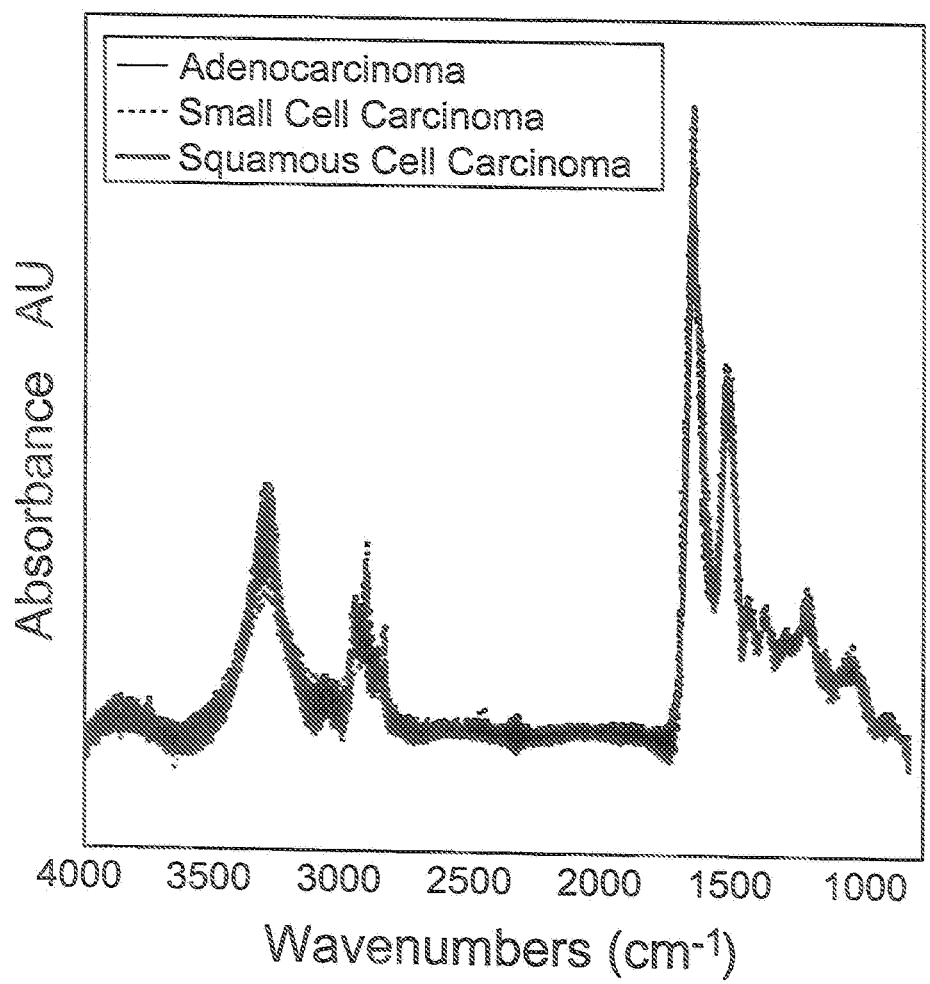
FIG. 19D shows KK transformed spectra calculated from spectra in FIG. 19C.
Figure 19E:
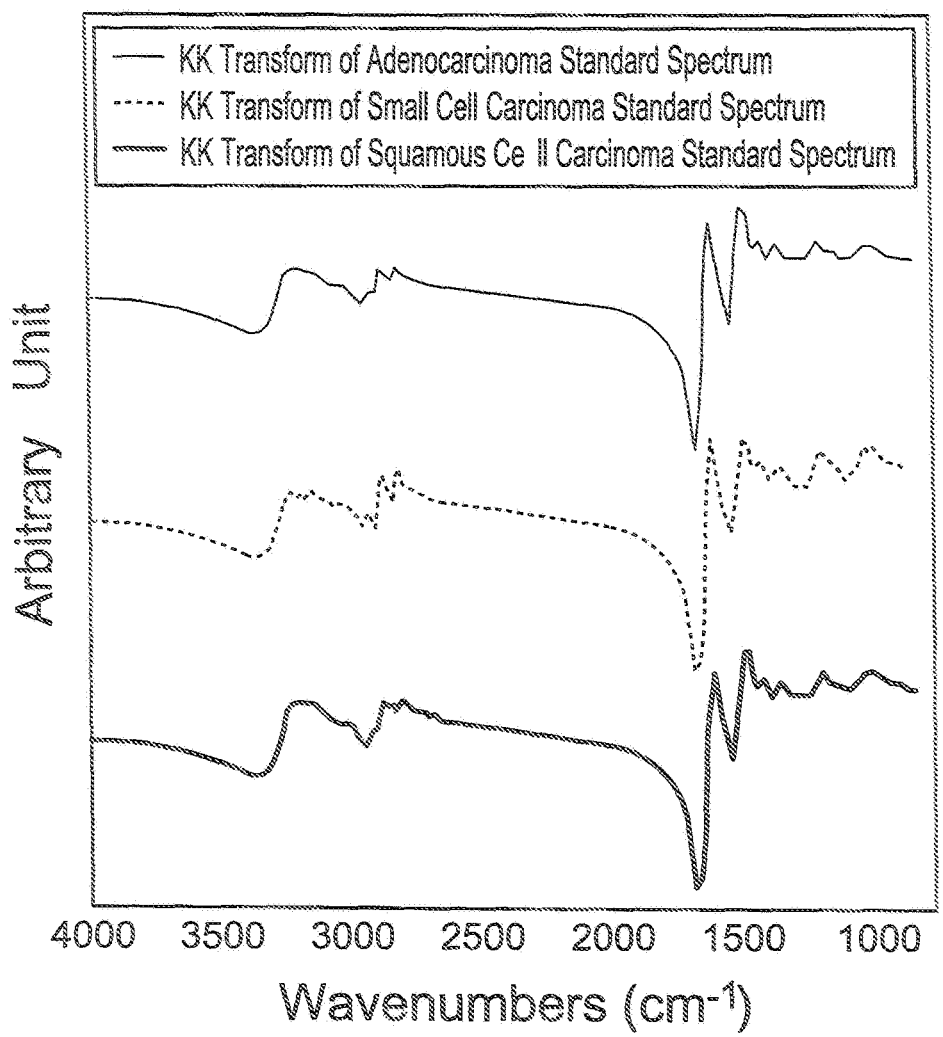
FIG. 19E shows PCA scores plots of the multi class data set before EMSC correction according to aspects of the invention.
Figure 19F:
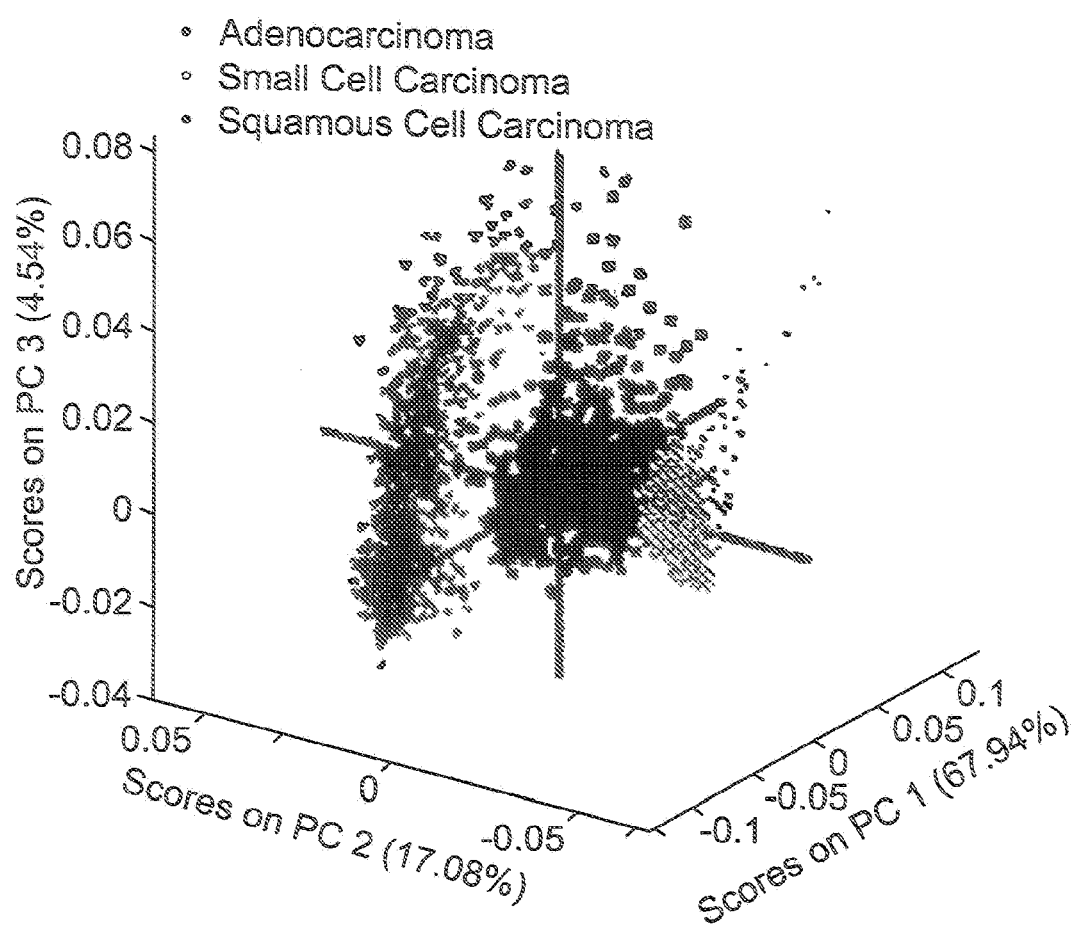
FIG. 19F shows PCA scores plots of the multi class data set after EMSC correction according to aspects of the invention.

A sub space model for Mie scattering contributions was constructed by calculating 340 Mie scattering curves that describe a nuclei sphere radius range of 6 μm-40 μm, and a refractive index range of 1.1-1.5, using the Van de Hulst approximation formulae (see, e.g., Brussard, et al., Rev. Mod. Phys., 34:507 (1962)). The first 10 principal components that describe over 95% of the variance composed in these scattering curves, were then used in a addition to the KK transforms for each cancer type, as interferences in a 1 step EMSC correction of data sets. The EMSC calculation took approximately 1 sec per 1000 spectra. FIG. 19D shows KK transformed spectra calculated from spectra in FIG. 19C. FIG. 19E shows PCA scores plots of the multi class data set before EMSC correction. FIG. 19F shows PCA scores plots of the multi class data set after EMSC correction. The analysis was performed on the vector normalized $1800\ cm^{-1}$-$900\ cm^{-1}$ spectral region.

Figure 20A:
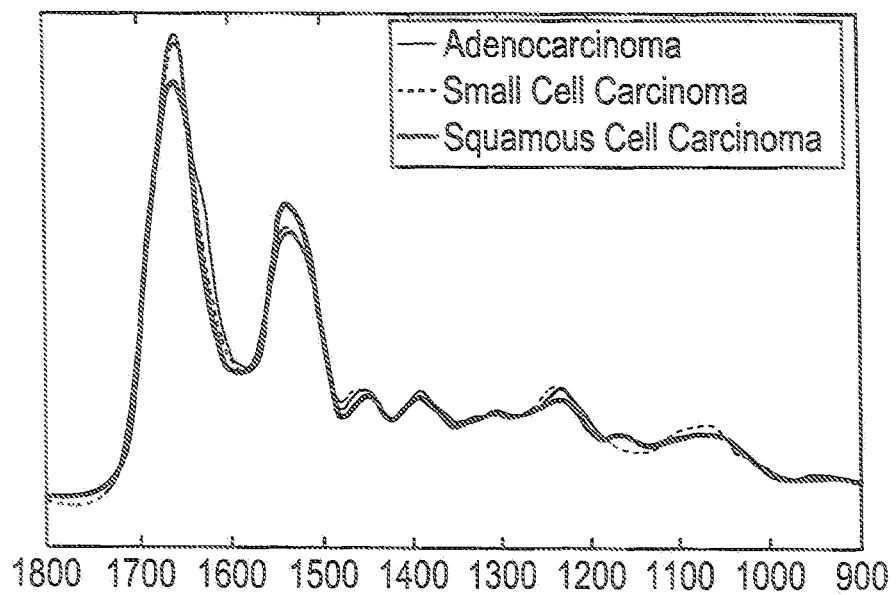
FIG. 20A shows mean absorbance spectra of lung adenocarcinoma, small cell carcinoma, and squamous carcinoma, according to aspects of the invention.
Figure 20B:
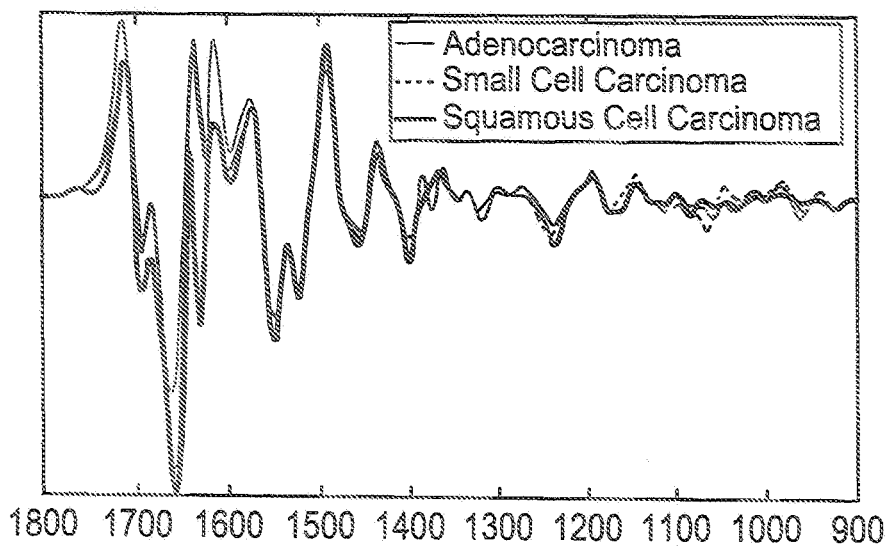
FIG. 20B shows second derivative spectra of absorbance spectra displayed in FIG. 20A according to aspects of the invention.

FIG. 20A shows mean absorbance spectra of lung adenocarcinoma, small cell carcinoma, and squamous carcinoma, respectively. These were calculated from 1000 scatter corrected cellular spectra of each cell type. FIG. 20B shows second derivative spectra of absorbance spectra displayed in FIG. 20A. In general, adenocarcinoma and squamous cell carcinoma have similar spectral profiles in the low wavenumber region of the spectrum. However, the squamous cell carcinoma displays a substantially low wavenumber shoulder for the amide I band, which has been observed for spectral data recorded from squamous cell carcinoma in the oral cavity (Papamarkakis, et al. (2010), Lab. Invest., 90:589-598). The small cell carcinoma displays very strong symmetric and anti-symmetric phosphate bands that are shifted slightly to higher wavenumber, indicating a strong contribution of phospholipids to the observed spectra.

Figure 21A:
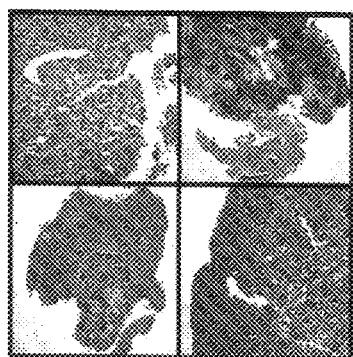
FIG. 21A shows 4 stitched microscopic R&E-stained images of 1 mm×1 mm tissue areas comprising adenocarcinoma, small cell carcinoma, and squamous cell carcinoma cells, respectively, according to aspects of the invention.
Figure 21B:
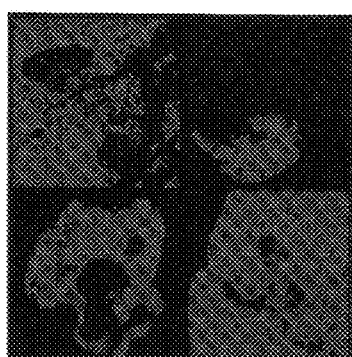
FIG. 21B is a binary mask image constructed by performance of a rapid reduced RCA analysis upon the 1350 $cm^{-1}$-900 $cm^{-1}$ spectral region of the 4 stitched raw infrared images recorded from the tissue areas shown in FIG. 21A according to aspects of the invention.
Figure 21C:
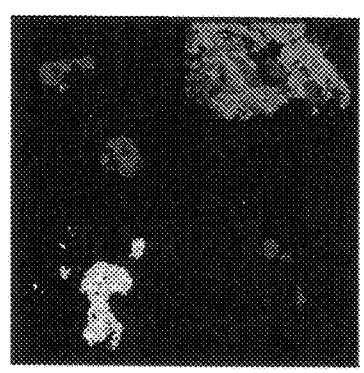
FIG. 21C is a 6-cluster RCA image of the scatter corrected spectral data recorded from regions of diagnostic cellular material according to aspects of the invention.

Since the majority of sample area is composed of blood and non-diagnostic material, the data was pre-processed to only include diagnostic material and correct for scattering contributions. In addition, HCA was used to create a binary mask and finally classify the data. This result is shown in FIGS. 21A-21C. FIG. 21A shows 4 stitched microscopic R&E-stained images of 1 mm×1 mm tissue areas comprising adenocarcinoma, small cell carcinoma, and squamous cell carcinoma cells, respectively. FIG. 21B is a binary mask image constructed by performance of a rapid reduced RCA analysis upon the $1350\ cm^{-1}$-$900\ cm^{-1}$ spectral region of the 4 stitched raw infrared images recorded from the tissue areas shown in FIG. 21A. The regions of diagnostic cellular material and blood cells are shown. FIG. 21C is a 6-cluster RCA image of the scatter corrected spectral data recorded from regions of diagnostic cellular material. The analysis was performed on the $1800\ cm^{-1}$-$900\ cm^{-1}$ spectral region. The regions of squamous cell carcinoma, adenicarcinoma, small cell carcinoma, and diverse desmoplastic tissue response are shown. Alternatively, these processes can be replaced with a supervised algorithm, such as an ANN.

The results presented in the Examples above show that the analysis of raw measured spectral data enables the differentiation of SCC and non-small cell carcinoma (NSCC). After the raw measured spectra are corrected for scattering contributions, adenocarinoma and squamous cell carcinoma according to methods in accordance with aspects of the invention, however, the two subtypes of NSCC, are clearly differentiated. Thus, these Examples provide strong evidence that this spectral imaging method may be used to identify and correctly classify the three main types of lung cancer.

Figure 22:
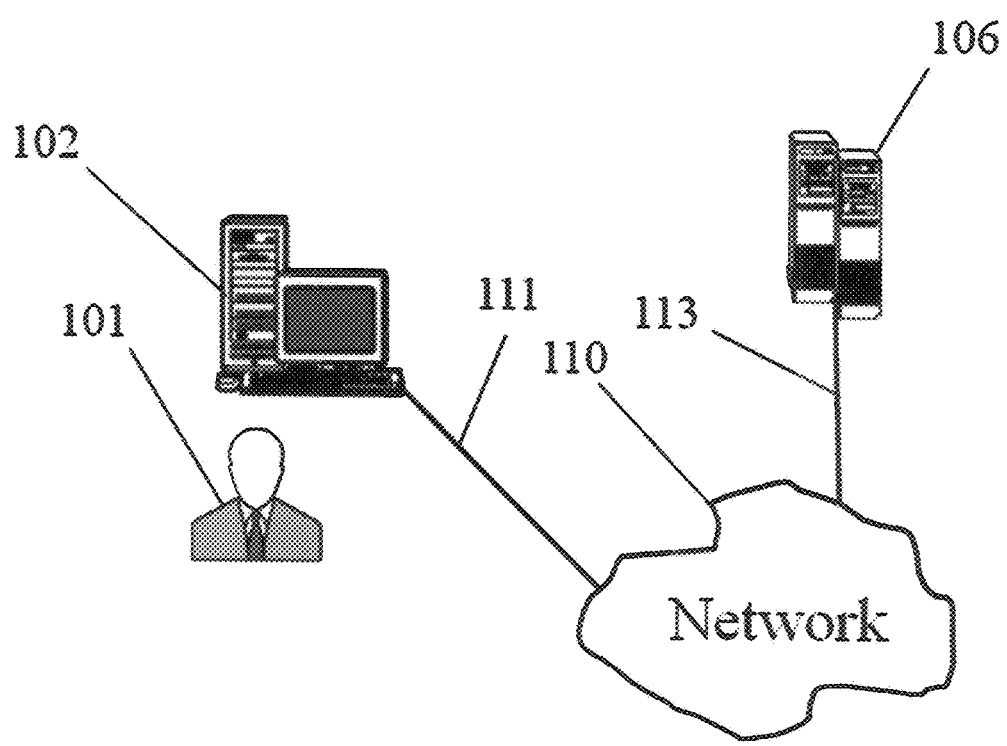
FIG. 22 shows various features of a computer system for use in conjunction with aspects of the invention.

FIG. 22 shows various features of an example computer system 100 for use in conjunction with methods in accordance with aspects of invention, including, but not limited to image registration and training. As shown in FIG. 22, the computer system 100 may be used by a requestor 101 via a terminal 102, such as a personal computer (PC), minicomputer, mainframe computer, microcomputer, telephone device, personal digital assistant (PDA), or other device having a processor and input capability. The server module may comprise, for example, a PC, minicomputer, mainframe computer, microcomputer, or other device having a processor and a repository for data or that is capable of accessing a repository of data. The server module 106 may be associated, for example, with an accessible repository of disease based data for use in diagnosis.

Information relating to a diagnosis, for example, via a network, 110, such as the Internet, for example, may be transmitted between the analyst 101 and the server module 106. Communications may be made, for example, via couplings 111, 113, such as wired, wireless, or fiberoptic links.

Figure 23:
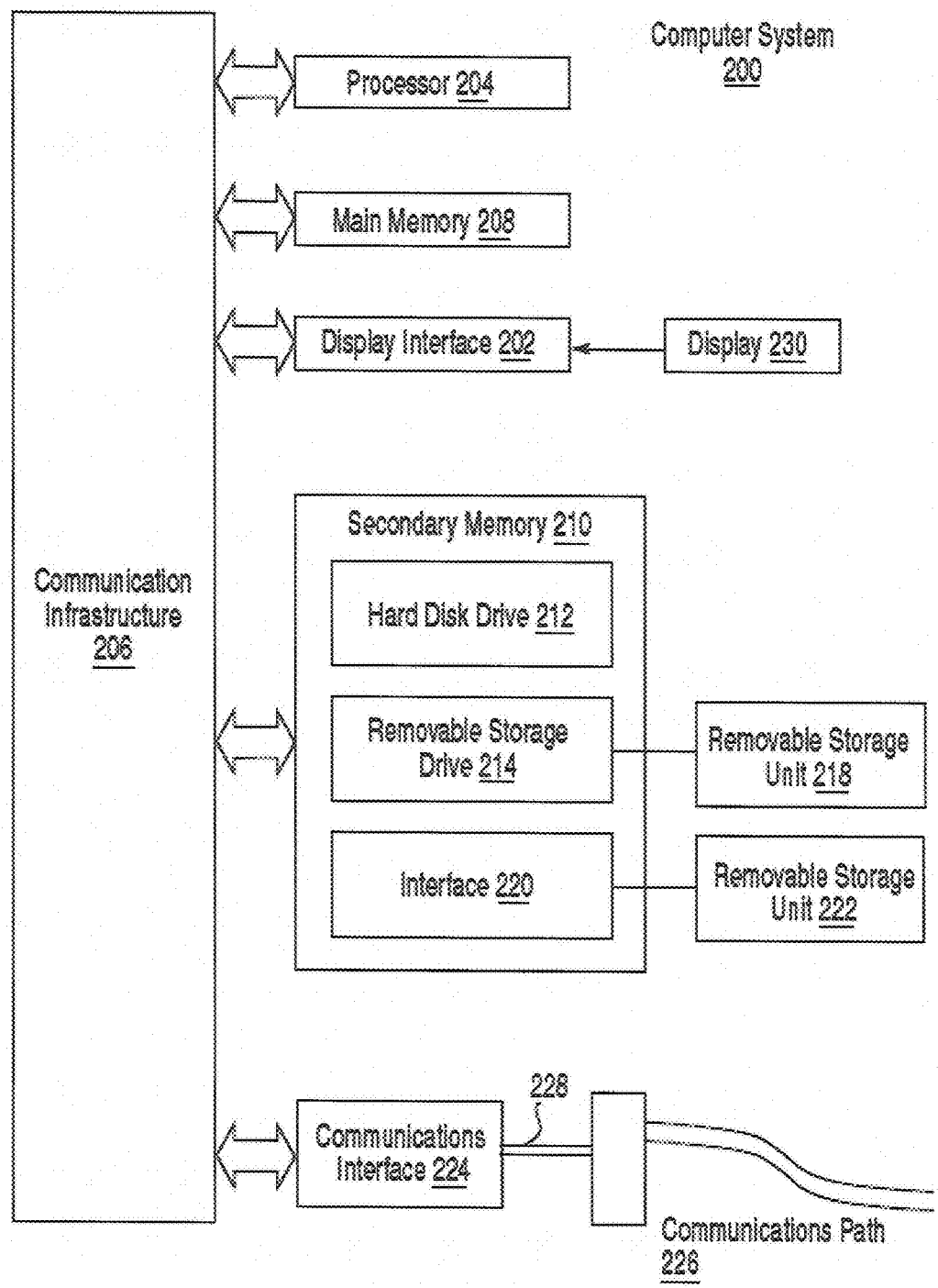
FIG. 23 shows a computer system for use in conjunction with aspects of the invention.

Aspects of the invention may be implemented using hardware, software or a combination thereof and may be implemented in one or more computer systems or other processing systems. In one variation, aspects of the invention are directed toward one or more computer systems capable of carrying out the functionality described herein. An example of such a computer system 200 is shown in FIG. 23.

Computer system 200 includes one or more processors, such as processor 204. The processor 204 is connected to a communication infrastructure 206 (e.g., a communications bus, cross-over bar, or network). Various software aspects are described in terms of this exemplary computer system. After reading this description, it will become apparent to a person skilled in the relevant art(s) how to implement the aspects of invention using other computer systems and/or architectures.

Computer system 200 can include a display interface 202 that forwards graphics, text, and other data from the communication infrastructure 206 (or from a frame buffer not shown) for display on the display unit 230. Computer system 200 also includes a main memory 208, preferably random access memory (RAM), and may also include a secondary memory 210. The secondary memory 210 may include, for example, a hard disk drive 212 and/or a removable storage drive 214, representing a floppy disk drive, a magnetic tape drive, an optical disk drive, etc. The removable storage drive 214 reads from and/or writes to a removable storage unit 218 in a well-known manner. Removable storage unit 218, represents a floppy disk, magnetic tape, optical disk, etc., which is read by and written to removable storage drive 214. As will be appreciated, the removable storage unit 218 includes a computer usable storage medium having stored therein computer software and/or data.

In alternative variations, secondary memory 210 may include other similar devices for allowing computer programs or other instructions to be loaded into computer system 200. Such devices may include, for example, a removable storage unit 222 and an interface 220. Examples of such may include a program cartridge and cartridge interface (such as that found in video game devices), a removable memory chip (such as an erasable programmable read only memory (EPROM), or programmable read only memory (PROM)) and associated socket, and other removable storage units 222 and interfaces 220, which allow software and data to be transferred from the removable storage unit 222 to computer system 200.

Computer system 200 may also include a communications interface 224. Communications interface 224 allows software and data to be transferred between computer system 200 and external devices. Examples of communications interface 224 may include a modem, a network interface (such as an Ethernet card), a communications port, a Personal Computer Memory Card International Association (PCMCIA) slot and card, etc. Software and data transferred via communications interface 224 are in the form of signals 228, which may be electronic, electromagnetic, optical or other signals capable of being received by communications interface 224. These signals 228 are provided to communications interface 224 via a communications path (e.g., channel) 226. This path 226 carries signals 228 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 214, a hard disk installed in hard disk drive 212, and signals 228. These computer program products provide software to the computer system 200. Aspects of the invention are directed to such computer program products.

Computer programs (also referred to as computer control logic) are stored in main memory 208 and/or secondary memory 210. Computer programs may also be received via communications interface 224. Such computer programs, when executed, enable the computer system 200 to perform the features in accordance with aspects of the invention, as discussed herein. In particular, the computer programs, when executed, enable the processor 204 to perform such features. Accordingly, such computer programs represent controllers of the computer system 200.

In a variation where aspects of the invention are implemented using software, the software may be stored in a computer program product and loaded into computer system 200 using removable storage drive 214, hard drive 212, or communications interface 224. The control logic (software), when executed by the processor 204, causes the processor 204 to perform the functions as described herein. In another variation, aspects of the invention are implemented primarily in hardware using, for example, hardware components, such as application specific integrated circuits (ASICs). Implementation of the hardware state machine so as to perform the functions described herein will be apparent to persons skilled in the relevant art(s).

In yet another variation, aspects of the invention are implemented using a combination of both hardware and software.

What is claimed is:

1. A method for registering a visual image and a spectral image of a biological sample, comprising:
    receiving a first set of coordinates of a plurality of reference marks on a slide or a slide holder with the biological sample and a visual image of the biological sample, wherein the first set of coordinates are independent from features within the visual image;
    associating the first set of coordinates with the visual image;
    receiving a second set of coordinates of the plurality of reference marks on the slide or the slide holder with the biological sample and a spectral image of the biological sample, wherein the second set of coordinates are independent from features within the spectral image;
    associating the second set of coordinates with the spectral image;
    creating a common coordinate system by associating the first set of coordinates and the second set of coordinates;
    generating a registered image with the spectral image and the visual image based upon the common coordinate system; and
    refining the registered image by applying one or more optimizations to the registered image.

2. The method of claim 1, wherein generating the registered image occurs automatically based upon the common coordinate system.

3. A system for registering a visual image and a spectral image of a biological sample, comprising:
    a processor;
    a user interface functioning via the processor; and
    a repository accessible by the processor;

wherein a first set of coordinates of a plurality of reference marks on a slide or a slide holder with the biological sample and a visual image are received and wherein the first set of coordinates are independent from features within the visual image;
wherein the first set of coordinates are associated with the visual image;
wherein a second set of coordinates of the plurality of reference marks on the slide or the slide holder with the biological sample and a spectral image are is received and wherein the second set of coordinates are independent from features within the spectral image;
wherein the second set of coordinates are associated with the spectral image;
wherein a common coordinate system is created by associating the first set of coordinates with the second set of coordinates;
wherein a registered image is generated with the spectral image and the visual image based upon the common coordinate system; and
wherein the registered image is refined by applying one or more optimizations to the registered image.

4. A non-transitory computer program product comprising a computer usable medium having control logic stored therein for causing a computer to register a visual image and a spectral image of a biological sample, the control logic comprising:
a set of codes for causing a computer to receive a first set of coordinates of a plurality of reference marks on a slide or a slide holder with the biological sample and a visual image of the biological sample, wherein the first set of coordinates are independent from features within the visual image;
a set of codes for causing the computer to associate the first set of coordinates with the visual image;
a set of codes for causing the computer to receive a second set of coordinates of the plurality of reference marks on the slide or the slide holder with the biological sample and a spectral image of the biological sample, wherein the second set of coordinates are independent from features within the spectral image;
a set of codes for causing the computer to associate the second set of coordinates with the spectral image;
a set of codes for causing the computer to create a common coordinate system by associating the first set of coordinates and the second set of coordinates;
a set of codes for causing the computer to generate a registered image with the spectral image and the visual image based upon the common coordinate system; and
a set of codes for causing the computer to refine the registered image by applying one or more optimizations to the registered image.

5. A method for image registration refinement, comprising:
receiving a spectral image of a biological sample and a visual image of the biological sample;
scaling the spectral image and the visual image, wherein the scaling is based upon a ratio between the spectral image and the visual image;
applying a first threshold value to the scaled spectral image and a second threshold value to the scaled visual image;
generating a binary spectral image based on the first threshold value;
generating a binary visual image based on the second threshold value;
aligning features of the spectral image with features of the visual image using the binary spectral image and the binary visual image;
refining an image registration of the spectral image and the visual image based upon the alignment of the features of the spectral image and the features of the visual image by applying one or more optimizations to the registered image relative to a selected metric that provides feedback for refining the registered image, wherein the image registration of the spectral image and the visual image is based upon a common coordinate system created by associating a first set of coordinates and a second set of coordinates; and
displaying a difference image illustrating an accuracy of the image registration,
wherein when the difference image indicates an error in the image registration, selecting different threshold values and updating the binary spectral image and the binary visual image based on the different threshold values.

6. The method of claim 5, wherein aligning the features of the spectral image and the features of the visual image improve the image registration of the spectral image and the visual image.

7. The method of claim 5, further comprising:
applying a weighted normalization to the spectral image to improve image features of the spectral image.

8. The method of claim 5, further comprising:
applying a morphological closure to the binary spectral image and the binary visual image.

9. The method of claim 5, further comprising:
softening the edges in the binary spectral image and the binary visual image.

10. The method of claim 5, further comprising:
minimizing the gray scale difference between the binary spectral image and the binary visual image.

11. A system for image registration refinement, comprising:
a processor;
a user interface functioning via the processor; and
a repository accessible by the processor;
wherein a spectral image of a biological sample and a visual image of the biological sample is received;
wherein the spectral image and the visual image are scaled based upon a ratio between the spectral image and the visual image;
wherein a first threshold value is applied to the scaled spectral image and a second threshold value is applied to the scaled visual image;
wherein a binary spectral image is generated based on the first threshold value;
wherein a binary visual image is generated based on the second threshold value;
wherein features of the spectral image are aligned with features of the visual image using the binary spectral image and the binary visual image;
wherein an image registration of the spectral image and the visual image is refined based upon the alignment of the features of the spectral image and the features of the visual image by applying one or more optimizations to the registered image relative to a selected metric that provides feedback for refining the registered image, wherein the image registration of the spectral image and the visual image is based upon a common coordinate system created by associating a first set of coordinates and a second set of coordinates;

wherein a difference image is displayed illustrating an accuracy of the image registration; and wherein different threshold values are selected when the difference image indicates an error in the image registration and the binary spectral image and the binary visual image are updated based on the different threshold values.

12. A non-transitory computer program product comprising a computer usable medium having control logic stored therein for causing a computer to refine a registered image, the control logic comprising:

a set of codes for causing a computer to receive a spectral image of a biological sample and a visual image of the biological sample;

a set of codes for causing a computer to scale to the spectral image and the visual image based upon a ratio between the spectral image and the visual image;

a set of codes for causing the computer to apply a first threshold value to the scaled spectral image and a second threshold value to the scaled visual image;

a set of codes for causing the computer to generate a binary spectral image based on the first threshold value;

a set of codes for causing the computer to generate a binary visual image based on the second threshold value;

a set of codes for causing the computer to align features of the spectral image with features of the visual image using the binary spectral image and the binary visual image;

a set of codes for causing the computer to refine an image registration of the spectral image and the visual image based upon the alignment of the features of the spectral image and the features of the visual image by applying one or more optimizations to the registered image relative to a selected metric that provides feedback for refining the registered image, wherein the image registration of the spectral image and the visual image is based upon a common coordinate system created by associating a first set of coordinates and a second set of coordinates; and a set of codes for causing the computer to display a difference image illustrating an accuracy of the image registration, wherein when the difference image indicates an error in the image registration, selecting different threshold values and updating the binary spectral image and the binary visual image based on the different threshold values.

13. The method of claim 1, wherein the one or more optimizations comprise one or more of a rigid body transform, minimizing a registration distance function between points in the registered image, and minimizing a least square among pairs of selected points in the spectral image and the visual image.

14. The method of claim 5, wherein the metric is generated by image based information.

15. The method of claim 1, wherein generating the registered image further comprises using the common coordinate system to digitally join pixels in the spectral image with corresponding pixels in the visual image.

16. The method of claim 5, further comprising: iteratively determining a preferred registration area.

* * * * *